(12) United States Patent
Lee et al.

(10) Patent No.: US 9,096,575 B2
(45) Date of Patent: Aug. 4, 2015

(54) GROUP 4 METAL COMPOUND CONTAINING THIOPHENE-FUSED CYCLOPENTADIENYL LIGAND DERIVED FROM TETRAQUINOLINE DERIVATIVE AND OLEFIN POLYMERIZATION USING THE SAME

(71) Applicant: Lotte Chemical Corporation, Seoul (KR)

(72) Inventors: Bun-Yeoul Lee, Gyeonggi-do (KR); Ji-Hae Park, Gyeonggi-do (KR); Seung-Hyun Do, Gyeonggi-do (KR)

(73) Assignee: Lotte Chemical Corporation, Seoul (KR)

( * ) Notice: Subject to any disclaimer, the term of this patent is extended or adjusted under 35 U.S.C. 154(b) by 0 days.

(21) Appl. No.: 14/495,256

(22) Filed: Sep. 24, 2014

(65) Prior Publication Data
US 2015/0011770 A1  Jan. 8, 2015

Related U.S. Application Data

(62) Division of application No. 13/640,924, filed as application No. PCT/KR2011/002580 on Apr. 12, 2011, now Pat. No. 8,912,352.

(30) Foreign Application Priority Data

Apr. 12, 2010  (KR) .................. 10-2010-0033273
Jun. 16, 2010  (KR) .................. 10-2010-0057102

(51) Int. Cl.
| | |
|---|---|
| C07D 409/04 | (2006.01) |
| C08F 4/6592 | (2006.01) |
| C07F 17/00 | (2006.01) |
| C08F 210/16 | (2006.01) |
| B01J 31/02 | (2006.01) |
| C07F 7/28 | (2006.01) |
| C08F 10/02 | (2006.01) |
| C08F 236/04 | (2006.01) |
| C08F 4/76 | (2006.01) |
| C08F 10/00 | (2006.01) |
| C08F 4/659 | (2006.01) |

(52) U.S. Cl.
CPC ........... *C07D 409/04* (2013.01); *B01J 31/0244* (2013.01); *C07F 7/28* (2013.01); *C07F 17/00* (2013.01); *C08F 4/6592* (2013.01); *C08F 4/76* (2013.01); *C08F 10/02* (2013.01); *C08F 210/16* (2013.01); *C08F 236/04* (2013.01); *C08F 4/65908* (2013.01); *C08F 4/65912* (2013.01); *C08F 10/00* (2013.01); *C08F 2420/02* (2013.01); *C08F 2420/06* (2013.01); *Y10S 526/943* (2013.01)

(58) Field of Classification Search
CPC .................................................. C07D 409/04
See application file for complete search history.

(56) References Cited

U.S. PATENT DOCUMENTS

| | | | |
|---|---|---|---|
| 6,451,938 B1 | 9/2002 | Fisher et al. | |
| 6,635,779 B1 | 10/2003 | Ewen et al. | |
| 7,972,987 B2 * | 7/2011 | Lee et al. ................. | 502/155 |
| 2004/0242880 A1 | 12/2004 | Mihan et al. | |
| 2005/0192418 A1 | 9/2005 | Ewen et al. | |
| 2005/0234204 A1 | 10/2005 | Resconi et al. | |
| 2007/0010637 A1 | 1/2007 | Lee et al. | |
| 2007/0010638 A1 | 1/2007 | Lee et al. | |
| 2007/0225158 A1 | 9/2007 | Lee et al. | |
| 2007/0260026 A1 | 11/2007 | Michiue et al. | |
| 2008/0027071 A1 | 1/2008 | Rottlander et al. | |
| 2010/0062927 A1 | 3/2010 | Lee et al. | |
| 2010/0130201 A1 | 5/2010 | Yu | |

FOREIGN PATENT DOCUMENTS

| | | |
|---|---|---|
| CN | 1310909 C | 4/2007 |
| CN | 101578293 A | 11/2009 |
| EP | 0 892 013 A1 | 1/1999 |
| EP | 1 739 103 A1 | 1/2007 |
| JP | 2001-512523 A | 8/2001 |
| JP | 2003-517010 A | 5/2003 |
| JP | 2005-538198 A | 12/2005 |
| JP | 2006-502076 A | 1/2006 |
| JP | 2006-513974 A | 4/2006 |
| JP | 2008-527050 A | 7/2008 |
| JP | 2008-222635 A | 9/2008 |

(Continued)

OTHER PUBLICATIONS

Cho, D. J., et al.; "*o-Phenylene-Bridged Cp/Amido Titanium Complexes for Ethylene/1-Hexene Copolymerizations*;" Organometallics, vol. 25, No. 9; pp. 2133-2134; dated Apr. 24, 2006; abstract retrieved on May 27, 2014 from <http://pubs.acs.org/doi/abs10.1021/om0601854>.

De Rosa, C., et al.; "*Metalloorganic Polymerization Catalysis as a Tool to Probe Crystallization Properties of Polymers: The Case of isotactic Poly(1-butene)*;" Angew. Chem. Int. Ed., vol. 48, No. 52; pp. 9871-; dated Dec. 21, 2009; abstract retrieved on May 28, 2014 from <http://onlinelibrary.wiley.com/doi/10.1002/anie.200904300/abstract>.

(Continued)

*Primary Examiner* — Caixia Lu
(74) *Attorney, Agent, or Firm* — Alston & Bird LLP

(57) ABSTRACT

The present invention relates to a novel ligand derived from a tetrahydroquinoline derivative, and a transition metal compound prepared using the ligand, where an amido ligand is linked to an ortho-phenylene ligand to form a condensed ring and a 5-membered cyclic pi-ligand linked to the ortho-phenylene ligand is fused with a heterocyclic thiophene ligand. Compared with the catalysts not fused with a heterocyclic thiophene ligand, the transition metal compound of the present invention as activated with a co-catalyst has higher catalytic activity in olefin polymerization and provides a polymer with higher molecular weight.

4 Claims, 1 Drawing Sheet

(56) References Cited

FOREIGN PATENT DOCUMENTS

| KR | 10-0354290 B1 | 1/2001 |
|---|---|---|
| KR | 10-2007-0096465 A | 10/2007 |
| KR | 10-0789241 B1 | 1/2008 |
| KR | 10-0789242 B1 | 1/2008 |
| KR | 10-0820542 B1 | 4/2008 |
| KR | 10-2008-0049981 A | 6/2008 |
| KR | 10-2008-0065868 A | 7/2008 |
| KR | 10-0843603 B1 | 7/2008 |
| KR | 10-2008-0070989 A | 8/2008 |
| KR | 10-2008-0101542 A | 11/2008 |
| KR | 10-0906165 B1 | 7/2009 |
| KR | 10-2010-0033273 A | 3/2010 |
| KR | 10-2010-0057102 A | 5/2010 |
| WO | WO-03/024982 A1 | 3/2003 |
| WO | WO-2006/022355 A | 3/2006 |
| WO | WO-2008/066266 A1 | 6/2008 |
| WO | WO 2008/084931 A1 | 7/2008 |

OTHER PUBLICATIONS

De Rosa, C., et al,; "*Structure—Property Correlations in Polypropylene from Metallocene Catalysts: Stereodefective, Regioregular Isotactic Polypropylene*;" J. Am. Chem. Soc., vol. 126, No. 51; pp. 17040-17049; dated Dec. 29, 2004; abstract retrieved on May 28, 2014 from <http://pubs.acs.org/doi/abs/10.1021/ja045684f>.

De Rosa, C., et al.; "*Synthesis and Characterization of High-Molecular-Weight Syndiotactic Amorphous Polypropylene*;" J. Am. Chem. Soc., vol. 125, No. 36; pp. 10913-10920; dated Sep. 10, 2003; abstract retrieved on May 28, 2014 from <http://pubs.acs.org/doi/abs/10.1021/ja035911y>.

Ewen, J. A., et al. "*Chiral Ansa Metallocenes with Cp Ring-Fused to Thiophenes and Pyrroles: Syntheses, Crystal Structures, and Isotactic Polypropylene Catalysts*;" J. Am. Chem. Soc.,vol. 123, No. 20; pp. 4763-4773; dated May 23, 2001; abstract retrieved on May 28, 2014 from <http://pubs.acs.org/doi/abs/10.1021/ja004266h>.

Ewen, J. A., et al.; "*Polymerization Catalysts with Cyclopentadienyl Ligands Ring-Fused to Pyrrole and Thiophene Heterocycles*;" J. Am. Chem. Soc., vol. 120, No. 41; pp. 10786-10787; dated Oct. 21, 1998; abstract retrieved on May 28, 2014 from <http://pubs.acs.org/doi/abs/10.1021/ja9823215>.

Ewen, J. A., et al.; "*Stereoblock Isotactic-Hemiisotactic Poly(propylene)s and Ethylene/Propylene Copolymers Obtained with ansa-Cyclopenta[1,2-b;4,3-b'] dithiophene Catalysts*;" Macromol. Chem. Phys., vol. 205, No. 3; pp. 302-307; dated Feb. 2004; abstract retrieved on May 28, 2014 from <http://onlinelibrary.wiley.com/doi/10.1002/macp.200300222/abstract>.

Grandini, C., et al.; "*Heterocycle-Fused Indenyl Silyl Amido Dimethyl Titanium Complexes as Catalysts for High Molecular Weight Syndiotactic Amorphous Polypropylene*;" Organometallics, vol. 23, No. 3; pp. 344-360; dated Feb. 2, 2004; Abstract abstract retrieved on May 27, 2014 from <http://pubs.acs.org/doi/abs/10.1021/om030543s>.

Joe, D. J., et al.; "*o-Phenylene-bridged Cp/sulfonamido titanium complexes for ethylene/1-octene copolymerization*;" Dalton Trans., No. 33; pp. 4056-4062; dated 2006; Abstract retrieved on May 27, 2014 from <http://pubs.rsc.org/en/content/articlelanding/2006/dt/b605345a#!divAbstract>.

Joung, U. G., et al.; "*Phenylene-Bridged Cp/Carboxamide Ligands for Titanium Complexes of Various Binding Modes and Their Ethylene/1-Octene Copolymerization*;" Organometallics, vol. 25, No. 21; pp. 5122-5130; dated Oct. 9, 2006; abstract retrieved on May 27, 2014 from <http://pubs.acs.org/doi/abs/10.1021/om060604x>.

Kaminsky et al.; "*New application for metallocene catalysts in olefin polymerization*;" Dalton Trans., No. 41 pp. 8803-8810; dated Aug. 27, 2009; abstract retrieved on May 27, 2014 from <http://pubs.rsc.org/en/content/articlelanding/2009/dt/b910542p#!divAbstract>.

Katritzky, A. R., et al.; "*Carbon dioxide: A reagent for the protection of nucleophilic centres and the simultaneous activation of alternative locations to electrophilic attack. : Part I. A new Synthetic method for the 2-substitution of 1-unsubstituted indoles*;" Tetrahedron Lett., vol. 26, No. 48; pp. 5935-5938; dated 1985; abstract retrieved on May 28, 2014.

Katritzky, A. R., et al.; "*Carbon dioxide: A reagent for the protection of nucleophilic centres and the simultaneous activation of electrophilic attack : Part II. A new synthetic method for the 1-substitution of 1,2.3, 4-tetrahydroisoquinolines*;" Tetrahedron, vol. 42, No. 9; pp. 2571-2574; dated 1986; abstract retrieved on May 28, 2014 from <http://www.sciencedirect.com/science/article/pii/0040402086800242>.

Lee, S. H., et al.; "*Bimetallic phenylene-bridged Cp/amide titanium complexes and their olefin polymerization*; " Dalton Trans. No. 40; pp. 4608-4614; dated 2007; abstract retrieved on May 27, 2014 from <http://pubs.rsc.org/en/content/articlelanding/2007/dt/b710017e#!divAbstract>.

Lee, S. H., et al.; "*o-Phenylene-bridged Cp/amido titanium and zirconium complexes and their polymerization reactivity*;" J. Organomet. Chem. vol. 693, No. 3; pp. 457-467; dated Feb. 1, 2008; abstract retrieved on May 27, 2014 from <http://www.sciencedirect.com/science/article/pii/S0022328X07008297>.

Lee, B. Y., et al.; "*Preparation of Anchored Metallocene Complexes on Dehydroxylated Silica and Their Use in the Polymerization of Ethylene*;" Macromolecues, vol. 33, No. 9; pp. 3194-3195; dated May 2, 2000; retrieved on May 28, 2014 from <https://www.researchgate.net/publication/231711882_Preparation_of_Anchored_Metallocene_Complexes_on_Dehydroxylated_Silica_and_Their_Use_in_the_Polymerization_of_Ethylene>.

Na, S. J., et al.; "*Copolymerization of 5,6-Dihydrodicyclopentadiene and Ethylene*;" Macromolecules, vol. 42, No. 11; pp. 4055-4057; dated Jun. 10, 2008; abstract retrieved on May 28, 2014 from <http://pubs.acs.org/doi/abs/10.1021/ma800380r>.

Nifant'ev, A. E., et al.; "*C1-Symmetric Heterocyclic Zirconocenes as Catalysts for Propylene Polymerization*, 1;" Macromol. Chem. Phys., vol. 205, No. 17; pp. 2275-2291; dated Nov. 26, 2004; abstract retrieved on May 28, 2014 from <http://onlinelibrary.wiley.com/doi/10.1002/macp.200400238/abstract>.

Park, J. H., et al.; "*Preparation of half-metallocenes of thiophene-fused and tetrahydroquinoline-linked cyclopentadienyl ligands for ethylene/ [alpha]-olefin copolymerization*", Dalton Transactions, vol. 39, No. 41, Sep. 21, 2010, p. 9994, Xp055090168, Issn: 1477-9226, Doi: 10.1039/C0dt00637h.

Ryabov, A. N., et al.; "*Constrained geometry complexes of titanium (IV) and zirconium (IV) involving cyclopentadienyl fused to thiophene ring*", Journal of Organometallic Chemistry, Elsevier-Sequoia S.A. Lausanne, Ch, vol. 690, No. 19, Aug. 5, 2005, pp. 4213-4221, XP027708856, ISSN: 0022-328X [retrieved on Oct. 1, 2005].

Resconi, L., et al.; "*C1-Symmetric Heterocyclic Zirconocenes as Catalysts for Propylene. Propylene Polymerization*, 2;" Macromol. Chem. Phys., vol. 206, No. 14; pp. 1405-1438; dated Jul. 21, 2005; abstract retrieved on May 28, 2014 from <http://onlinelibrary.wiley.com/doi/10.1002/macp.200400533/abstract>.

Senda, T., et al.; "*Titanium Complexes of Silicon-Bridged Cyclopentadienyl-Phenoxy Ligands Modified with Fused-Thiophene: Synthesis, Characterization, and Their Catalytic Performance in Copolymerization of Ethylene and 1-Hexene*", Organometallics, vol. 28, No. 24, Dec. 28, 2009, pp. 6915-6926, Xp055090319, ISSN: 0276-7333, Doi: 10.1021/Om900853q.

Wu, C. J., et al.; "*CO2-Mediated ortho-Lithiation of N-Alkylanilines and Its Use for the Contruction of Polymerization Catalysts*;" Organometallics, vol. 27, No. 15; pp. 3907-3917; dated Aug. 11, 2008; abstract retrieved on May 27, 2014 from <http://pubs.acs.org/doi/abs/10.1021/om800317v>.

Wu, C. J., et al.; "*Ortho Lithiation of Tetrahydroquinoline Derivatives and Its [sic] Use for the Facile Construction of Polymerization Catalysts*;" Organometallics, vol. 26, No. 27, Dec. 31, 2007, pp. 6685-6687, Xp008151338.

Wu, C. J., et al.; "*Synthesis and structures of o-phenylene-bridged Cp/phosphinoamide titanium complexes*;" J. Organomet. Chem., vol. 691, No. 26; pp. 5626-5634; dated Dec. 15, 2006; abstract retrieved on May 27, 2014 from <http://www.sciencedirect.com/science/article/pii/S0022328X06007625>.

(56) References Cited

OTHER PUBLICATIONS

Yu, S. T., et al.; "*Preparation of a Bulky Cycloolefin/Ethylene Copolymer and Its Tensile Properties*;" Macromolecules, vol. 43, No. 2; pp. 725-730; dated Jan. 26, 2010; abstract retrieved on May 28, 2014 from <http://pubs.acs.org/doi/abs/10.1021/ma902334d>.
Extended European Search Report for Application No. 11769055.2; dated Dec. 10, 2013.
International Preliminary Report on Patentability for Application No. PCT/KR2011/002580; dated Oct. 16, 2012.
International Preliminary Report on Patentability for Application No. PCT/KR2011/002581; dated Oct. 16, 2012.
International Preliminary Report on Patentability for Application No. PCT/KR2011/002583; dated Oct. 16, 2012.
International Preliminary Report on Patentability for Application No. PCT/KR2011/002584; dated Oct. 16, 2012.
International Preliminary Report on Patentability for Application No. PCT/KR2011/002585; dated Oct. 16, 2012.
International Search Report and Written Opinion for Application No. PCT/KR2011/002581; dated Jan. 19, 2012.
International Search Report and Written Opinion for Application No. PCT/KR2011/002583; dated Jan. 19, 2012.
International Search Report and Written Opinion for Application No. PCT/KR2011/002584; dated Jan. 19, 2012.
International Search Report and Written Opinion for Application No. PCT/KR2011/002585; dated Jan. 19, 2012.
International Written Opinion for Application No. PCT/KR2011/002580; dated Dec. 26, 2011.
*J. Chem. Sc. Perkin Trans*. 1989, 16.
Office Action for Chinese Application No. 201180018710.1; dated Apr. 16, 2014.
Office Action for European Application No. 11769059.4; dated Jan. 10, 2014.
Office Action for Japanese Application No. 2013-503703; dated Feb. 4, 2014.
Extended European Search Report for Application No. 11769056.0; dated Dec. 11, 2013.
Extended European Search Report for Application No. 11769059.4; dated Dec. 10, 2013.
Extended European Search Report for Application No. 11769060.2; dated Dec. 10, 2013.
Office Action for Chinese Application No. 201180018685.7; dated Dec. 4, 2013.
Office Action for Chinese Application No. 201180018695.0; dated Jan. 6, 2014.
Office Action for European Application No. 11769056.0; dated Jan. 7, 2013.
Office Action for European Application No. 11769060.2; dated Jan. 15, 2014.
Office Action for Japanese Application No. 2013-504820; dated Feb. 4, 2014.
Office Action for Korean Application No. 10-2011-0033623; dated Apr. 1, 2014.
Office Action for Korean Application No. 10-2011-0033625; dated Apr. 1, 2014.
Office Action for Korean Application No. 10-2011-0033626; dated Apr. 1, 2014.
Office Action for European Application No. 11 769 056.0 dated Sep. 17, 2014.
Office Action for European Application No. 11 769 058.6 dated Sep. 17, 2014.
Office Action for European Application No. 11 769 060.2 dated Sep. 17, 2014.
Office Action for European Application No. 11 769 055.2 dated Sep. 17, 2014.
Office Action for European Application No. 11 769 059.4 dated Sep. 17, 2014.
Bryliakov, K. P. et al., *Nasa-Titanocene Catalysts for Alpha-Olefin Polymerization, Syntheses, Structures, and Reactions with Methylaluminoxane and Boron-Based Activators*, Organometallics, ACS, vol. 24, No. 5 (Feb. 28, 2005), pp. 894-904 (XP00904851).
International Search Report for Application No. PCT/KR2011/002580 (7 pages) dated Dec. 26, 2011.
Ryabov, Alexey N. et al; "Zirconium Complexes with Cyclopentadienyl Ligands Involving Fused A Thiophene Fragment"; Organometallics; vol. 21; pp. 2842-2855; dated Jun. 8, 2002 (14 pages).

* cited by examiner

GROUP 4 METAL COMPOUND CONTAINING THIOPHENE-FUSED CYCLOPENTADIENYL LIGAND DERIVED FROM TETRAQUINOLINE DERIVATIVE AND OLEFIN POLYMERIZATION USING THE SAME

CROSS-REFERENCE TO RELATED APPLICATIONS

This application claims the benefit of priority from and is a divisional of U.S. Ser. No. 13/640,924, filed Apr. 24, 2013, which claims the benefit of priority from and is a National Stage Entry of PCT/KR2011/002580, filed Apr. 12, 2011, which claims the benefit of priority from Korean applications 10-2010-0033273, filed Apr. 12, 2010, and 10-2010-0057102, filed Jun. 16, 2010, the entire contents of which are hereby incorporated.

FIELD OF THE INVENTION

The present invention relates to a novel transition metal compound containing a thiophene-fused cyclopentadienyl moiety substituted at the 8-position of a tetrahydroquinoline derivative and a method for preparing an olefin polymer using the same, and more particularly to a novel transition metal compound having a cyclopentadienyl/amido group bridged by an ortho-phenylene group and a method for preparing an olefin polymer using the same.

BACKGROUND OF THE INVENTION

The early synthesis method for olefin polymer involves preparing a boron compound of cyclopentenone and using the Suzuki-coupling reaction, as shown in the following Scheme 1. This method is, however, problematic in that the boron compound is hard to synthesize, making the synthesis method unsuitable for large-scaled manufacture, and that only a limited range of boron compounds can be prepared, consequently with difficulty in diversification of cyclopentadienyl ligands (*Organometallics* 2006, 25, 2133; *Dalton Trans.* 2006, 4056; *Organometallics* 2006, 25, 5122; *Dalton Trans.* 2007, 4608; *Organomet. Chem.* 2008, 693, 457; *J. Organomet. Chem.* 2006, 691, 5626; Korean Patent Registration No. 10-843603; Korean Patent Registration No. 10-0789241; Korean Patent Registration No. 10-0789242; and Korean Patent Registration No. 10-0843603).

[Scheme 1]

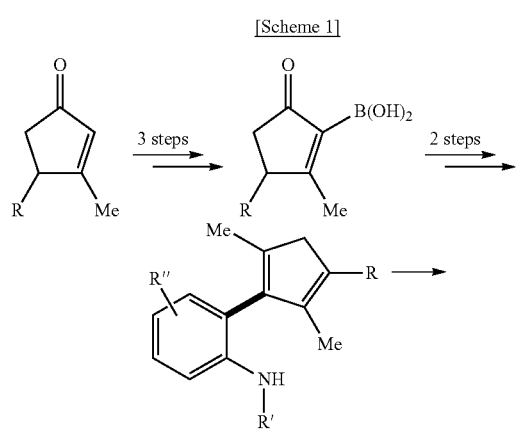

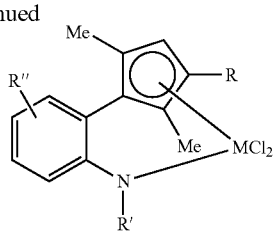

R = H or Me

To solve this problem, there has been developed a new synthesis method given by the following Scheme 2. The synthesis method in the Scheme 2 advantageously provides an approach to preparing the desired ligand in a single step and introduces a variety of 5-membered cyclic pi-ligands, such as indenyl or fluorenyl (*Organometaalics*, 2008, 27, 3907).

[Scheme 2]

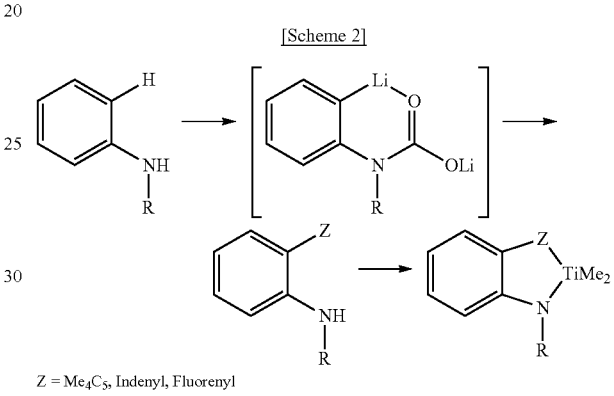

$Z = Me_4C_5$, Indenyl, Fluorenyl

The following compound 1 or 2 prepared by this method is superior to the conventional CGC([Me$_2$Si($\eta^5$-Me$_4$C$_5$)(N$^t$Bu)]TiCl$_2$) catalyst developed by Dow Chemical Corp. in terms of catalytic activity and copolymerization characteristic, showing the possibility of its use in the commercial manufacture process (*Organometallics*, 2007, 27, 6685; *Macromolecules*, 2008, 42, 4055; *Macromolecules*, 2010, 43, 725; Korean Patent Registration No. 820, 542; Korean Public Patent No. 08-0065868; and Korean Patent Registration No. 906,165). More specifically, the amido ligand is combined with the ortho-phenylene ligand to form a condensed ring, which reduces the steric hindrance at the reaction site of titanium to enhance reactivity.

[Compound 1 or 2]

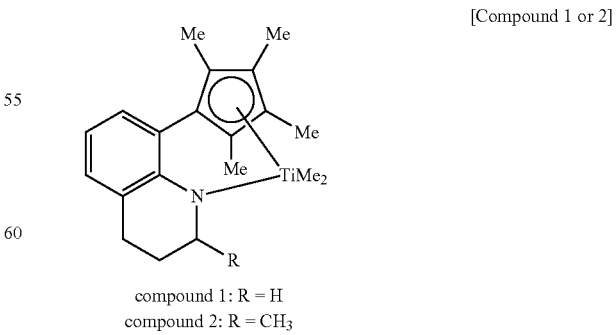

compound 1: R = H
compound 2: R = CH$_3$

Besides, transition metal compounds of 5-membered cyclic pi-ligands fused with a heterocyclic compound containing nitrogen or sulfur atom(s), and an olefin polymerization reaction using the transition metal compounds have been occasionally reported. But, there has never been a report on the transition metal compounds coordinated with 5-membered cyclic pi-ligands fused with a heterocyclic compound among those compounds having a condensed ring formed with an amido ligand and an ortho-phenylene ligand like compound 1 or 2 (*J. Am. Chem. Soc.*, 1998, 120, 10786; *J. Am. Chem. Soc.*, 2001, 123, 4763; *Macromol. Chem. Phys.*, 2004, 205, 302; Angew. Chem. Int. Ed., 2009, 48, 9871; *Organometallics*, 2002, 21, 2842; *J. Am. Chem. Soc.*, 2004, 126, 17040; *Macromol. Chem. Phys.*, 2004, 205, 2275; *Macromol. Chem. Phys.*, 2005, 206, 1405. *Organometallics*, 2004, 23, 344; *J. Am. Chem. Soc.*, 2003, 125, 10913; *Organometallics*, 2009, 28, 6915; *J. Organomet. Chem.*, 2005, 690, 4213; and U.S. Pat. No. 6,451,938).

Sustainable attempts have been made in the fields of academy and industry to develop homogenous Ziegler-Natta catalysts since Prof. Kaminsky developed the homogeneous Ziegler-Natta catalyst using a Group 4 metallocene compound activated with a methylaluminoxane co-catalyst in the late 1970's (Kaminsky et al., *Dalton Trans.*, 2009, 8803). It is the advantage claimed for the homogenous Ziegler-Natta catalysts over the heterogeneous Ziegler-Natta catalysts that the homogeneous Ziegler-Natta catalysts are excellent in $\alpha$-olefin incorporation in ethylene/$\alpha$-olefin copolymerization and provide a uniform $\alpha$-olefin distribution. The conventional heterogeneous catalysts in ethylene/$\alpha$-olefin copolymerization not only provide a low quantity of $\alpha$-olefin incorporation but cause the $\alpha$-olefin incorporation to occur primarily in the polymer chain with low molecular weight only. On the other hand, the disadvantage of the homogeneous catalysts is that they cannot provide a polymer with high molecular weight. In contrast to the conventional heterogeneous Ziegler-Natta catalysts which are used to form a polymer chain with high molecular weight, the homogeneous catalysts can be used only to produce a polymer chain with a molecular weight of no more than about 100,000. With low molecular weight, the polymers encounter a limitation in development of their usage, such as being inapplicable to the products required to have high strength. For that reason, the conventional heterogeneous Ziegler-Natta catalysts have been used in the industrial manufacture of polymers, and the use of the homogeneous catalysts is confined to the manufacture for some grades of polymer. It is therefore the ultimate object to overcome such a fundamental limitation by developing a homogeneous catalyst excellent in $\alpha$-olefin reactivity and capable of producing polymers with high molecular weight.

In an attempt to solve the problems with the prior art, the inventors of the present invention have discovered a novel ligand in which an amido ligand is linked to an ortho-phenylene ligand to form a condensed ring, and a 5-membered pi-ligand combined with the ortho-phenylene ligand is fused with a heterocyclic thiophene ligand, and found it out that the catalyst comprising a transition metal compound prepared from the novel ligand has higher catalytic activity and provides a polymer with higher molecular weight than the catalyst not fused with a heterocyclic thiophene ligand, thereby completing the present invention.

DISCLOSURE OF INVENTION

Technical Problem

It is therefore a first object of the present invention to provide a novel transition metal compound which contains fused ring with a heterocyclic thiophene ligand.

It is a second object of the present invention to provide a precursor for the transition metal compound that is the novel ligand.

It is a third object of the present invention to provide a method for preparing a precursor for the transition metal compound.

It is a fourth object of the present invention to provide a catalyst composition comprising the novel transition metal compound.

It is a fifth object of the present invention to provide a method for preparing an olefin polymer using the novel transition metal compound.

Technical Solution

To achieve the first object of the present invention, there is provided a transition metal compound represented by the following formula 1:

[Formula 1]

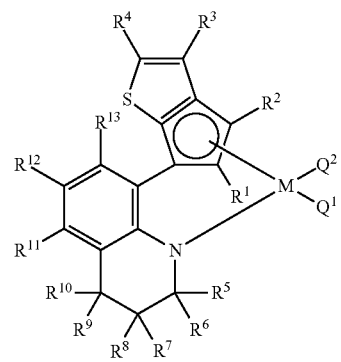

In the formula 1, M is a Group 4 transition metal;

$Q^1$ and $Q^2$ are independently halogen, $C_1$-$C_{20}$ alkyl, $C_2$-$C_{20}$ alkenyl, $C_2$-$C_{20}$ alkynyl, $C_6$-$C_{20}$ aryl, $C_1$-$C_{20}$ alkyl $C_6$-$C_{20}$ aryl, $C_6$-$C_{20}$ aryl $C_1$-$C_{20}$ alkyl, $C_1$-$C_{20}$ alkylamido, $C_6$-$C_{20}$ arylamido, or $C_1$-$C_{20}$ alkylidene;

$R^1$, $R^2$, $R^3$, $R^4$, $R^5$, $R^6$, $R^7$, $R^8$, $R^9$, and $R^{10}$ are independently hydrogen; $C_1$-$C_{20}$ alkyl with or without an acetal, ketal, or ether group; $C_2$-$C_{20}$ alkenyl with or without an acetal, ketal, or ether group; $C_1$-$C_{20}$ alkyl $C_6$-$C_{20}$ aryl with or without an acetal, ketal, or ether group; $C_6$-$C_{20}$ aryl $C_1$-$C_{20}$ alkyl with or without an acetal, ketal, or ether group; or $C_1$-$C_{20}$ silyl with or without an acetal, ketal, or ether group, where $R^1$ and $R^2$ can be linked to each other to form a ring; $R^3$ and $R^4$ can be linked to each other to foam a ring; and at least two of $R^5$ to $R^{10}$ can be linked to each other to form a ring; and $R^{11}$, $R^{12}$, and $R^{13}$ are independently hydrogen; $C_1$-$C_{20}$ alkyl with or without an acetal, ketal, or ether group; $C_2$-$C_{20}$ alkenyl with or without an acetal, ketal, or ether group; $C_1$-$C_{20}$ alkyl $C_6$-$C_{20}$ aryl with or without an acetal, ketal, or ether group; $C_6$-$C_{20}$ aryl $C_1$-$C_{20}$ alkyl with or without an acetal, ketal, or ether group; $C_1$-$C_{20}$ silyl with or without an acetal, ketal, or ether group; $C_1$-$C_{20}$ alkoxy; or $C_6$-$C_{20}$ aryloxy, where $R^{11}$ and $R^{12}$, or $R^{12}$ and $R^{13}$ can be linked to each other to form a ring.

To achieve the second object of the present invention, there is provided a precursor for the transition metal compound of the formula 1 as represented by the following formula 2:

[Formula 2]

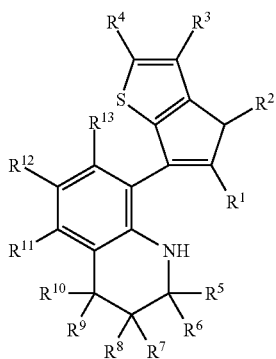

In the formula 2, $R^1$, $R^2$, $R^3$, $R^4$, $R^5$, $R^6$, $R^7$, $R^8$, $R^9$, $R^{10}$, $R^{11}$, $R^{12}$ and $R^{13}$ are as defined above.

To achieve the third object of the present invention, there is provided a method for preparing a precursor for transition metal compound as represented by the following formula 2, the method comprising: (a) reacting a tetrahydroquinoline derivative represented by the following formula 3 with alkyl lithium and adding carbon dioxide to prepare a compound represented by the following formula 4; and (b) reacting the compound of the formula 4 with alkyl lithium, adding a compound represented by the following formula 5, and then treating with an acid:

[Formula 2]

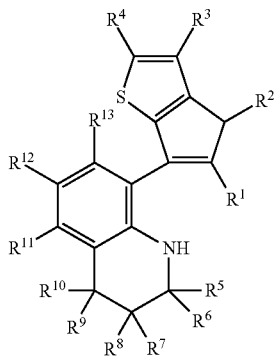

(Formula 3)

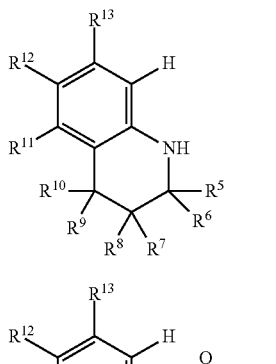

(Formula 4)

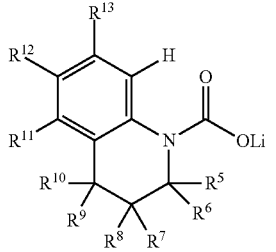

(Formula 5)

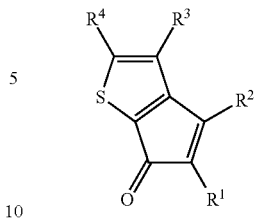

In the formulas 2, 3, 4 and 5, $R^1$, $R^2$, $R^3$, $R^4$, $R^5$, $R^6$, $R^7$, $R^8$, $R^9$, $R^{10}$, $R^{11}$, $R^{12}$, $R^{13}$ are as defined above.

To achieve the fourth object of the present invention, there is provided a catalyst composition comprising: a transition metal compound represented by the following formula 1; and at least one co-catalyst compound selected from the group consisting of compounds represented by the following formula 6, 7, or 8:

[Formula 1]

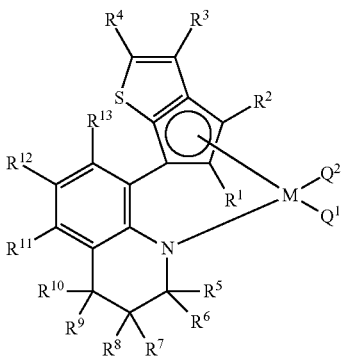

In the formula 1, M, $Q^1$, $Q^2$, $R^1$, $R^2$, $R^3$, $R^4$, $R^5$, $R^6$, $R^7$, $R^8$, $R^9$, $R^{10}$, $R^{11}$, $R^{12}$, and $R^{13}$ are as defined above.

$$—[Al(R^{61})—O]_a—$$ [Formula 6]

In the formula 6, $R^{61}$ is independently a halogen radical, a $C_1$-$C_{20}$ hydrocarbyl radical, or a halogen-substituted $C_1$-$C_{20}$ hydrocarbyl radical; and a is an integer of 2 or above.

$$D(R^{71})_3$$ [Formula 7]

In the formula 7, D is aluminum (Al) or boron (B); and $R^{71}$ is independently a halogen radical, a $C_1$-$C_{20}$ hydrocarbyl radical, or a halogen-substituted $C_1$-$C_{20}$ hydrocarbyl radical.

$$[L\text{-}H]^+[Z(A)_4]^- \text{ or } [L]^+[Z(A)_4]^-$$ [Formula 8]

In the formula 8, L is a neutral or cationic Lewis acid; Z is a Group 13 element; and A is independently a $C_6$-$C_{20}$ aryl or $C_1$-$C_{20}$ alkyl radical having at least one hydrogen atom substituted with a halogen radical, a $C_1$-$C_{20}$ hydrocarbyl radical, a $C_1$-$C_{20}$ alkoxy radical, or a $C_6$-$C_{20}$ aryloxy radical.

To achieve the fifth object of the present invention, there is provided a method for preparing a polyolefin by polymerizing an olefin-based monomer in the presence of the catalyst composition.

Advantageous Effects

When activated with the known co-catalyst, the novel transition metal compound provided by the present invention exhibits high catalytic activity and good copolymerization characteristic in olefin polymerization, resulting in production of a polymer with high molecular weight, so it can be readily used in commercial manufacture to prepare a polymer of different grades. Particularly, the transition metal compound of the present invention is advantageous over the catalysts not fused with a heterocyclic thiophene ligand in that it has higher catalytic activity and provides a polymer with higher molecular weight.

DETAILED DESCRIPTION OF THE INVENTION

Figure 1:
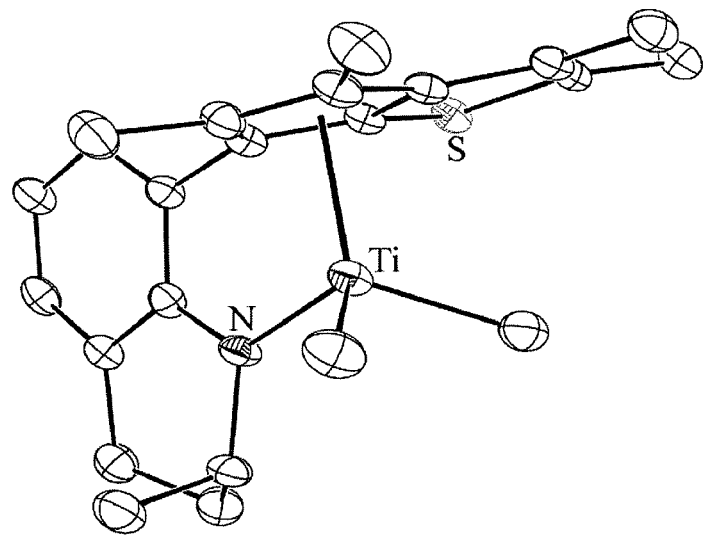
FIG. 1 is an illustration showing the structure of a transition metal compound (the compound E-4 of Example 9) according to one embodiment of the present invention.

Hereinafter, a description will be given as to a catalyst for olefin polymerization, and a method for preparing a polyolefin using the same according to the embodiments of the present invention.

In the course of repeated studies on catalysts for olefin polymerization, the inventors of the present invention have discovered a novel ligand in which an amido ligand is linked to an ortho-phenylene ligand to form a condensed ring, and a 5-membered cyclic pi-ligand linked to the ortho-phenylene ligand is fused with a heterocyclic thiophene ligand. Also, they have found it out that a transition metal compound comprising the ligand exhibits higher catalytic activity and provides a polymer with higher molecular weight than a transition metal compound not fused with a heterocyclic thiophene ligand.

In accordance with one embodiment of the present invention, there is provided a transition metal compound represented by the following formula 1:

[Formula 1]

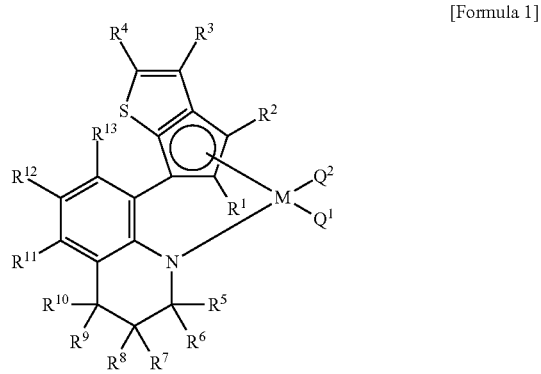

In the formula 1, M is a Group 4 transition metal; $Q^1$ and $Q^2$ are independently a halogen, $C_1$-$C_{20}$ alkyl, $C_2$-$C_{20}$ alkenyl, $C_2$-$C_{20}$ alkynyl, $C_6$-$C_{20}$ aryl, $C_1$-$C_{20}$ alkyl $C_6$-$C_{20}$ aryl, $C_6$-$C_{20}$ aryl $C_1$-$C_{20}$ alkyl, $C_1$-$C_{20}$ alkylamido, $C_6$-$C_{20}$ arylamido, or $C_1$-$C_{20}$ alkylidene;

$R^1$, $R^2$, $R^3$, $R^4$, $R^5$, $R^6$, $R^7$, $R^8$, $R^9$, and $R^{10}$ are independently hydrogen; $C_1$-$C_{20}$ alkyl with or without an acetal, ketal, or ether group; $C_2$-$C_{20}$ alkenyl with or without an acetal, ketal, or ether group; $C_1$-$C_{20}$ alkyl $C_6$-$C_{20}$ aryl with or without an acetal, ketal, or ether group; $C_6$-$C_{20}$ aryl $C_1$-$C_{20}$ alkyl with or without an acetal, ketal, or ether group; or $C_1$-$C_{20}$ silyl with or without an acetal, ketal, or ether group, where $R^1$ and $R^2$ can be linked to each other to form a ring; $R^3$ and $R^4$ can be linked to each other to form a ring; and at least two of $R^5$ to $R^{10}$ can be linked to each other to form a ring; and $R^{11}$, $R^{12}$, and $R^{13}$ are independently hydrogen; $C_1$-$C_{20}$ alkyl with or without an acetal, ketal, or ether group; $C_2$-$C_{20}$ alkenyl with or without an acetal, ketal, or ether group; $C_1$-$C_{20}$ alkyl $C_6$-$C_{20}$ aryl with or without an acetal, ketal, or ether group; $C_6$-$C_{20}$ aryl $C_1$-$C_{20}$ alkyl with or without an acetal, ketal, or ether group; $C_1$-$C_{20}$ silyl with or without an acetal, ketal, or ether group; $C_1$-$C_{20}$ alkoxy; or $C_6$-$C_{20}$ aryloxy, where $R^{11}$ and $R^{12}$, or $R^{12}$ and $R^{13}$ can be linked to each other to form a ring.

With a substituent, including an acetal group, a ketal group, or an ether group, $R^1$, $R^2$, $R^3$, $R^4$, $R^5$, $R^6$, $R^7$, $R^8$, $R^9$, $R^{10}$, $R^{11}$, $R^{12}$, and $R^{13}$ are useful in the preparation of a silica-supported catalyst, as disclosed in Korean Patent Registration No. 354,290 and *Macromolecules* 2000, 33, 3194. The use of at least one functional group selected from acetal, ketal, and ether groups does not interfere with the catalyst synthesis method of the present invention.

Compared with the catalyst not fused with a heterocyclic thiophene ligand, the catalyst for olefin polymerization using the transition metal compound represented by the formula 1 has higher catalytic activity to reduce the cost for catalysts in the preparation of resins and enables production of a polymer with higher molecular weight without significant deterioration in the α-olefin copolymerization characteristics. Such a catalyst having good α-olefin copolymerization characteristics and providing a polymer chain with high molecular weight is the ultimate aim of the development of homogeneous catalysts. With the development of olefin polymerization catalysts using the transition metal compound of the formula 1, it is possible to prepare polyolefin grades with various properties, which cannot be synthesized with the existing heterogeneous catalysts.

In the transition metal compound represented by the formula 1, M is preferably titanium (Ti), zirconium (Zr), or hafnium (Hf).

Preferably, $Q^1$ and $Q^2$ are independently halogen or $C_1$-$C_{20}$ alkyl. More preferably, $Q^1$ and $Q^2$ are independently chlorine or methyl.

$R^1$, $R^2$, $R^3$, $R^4$, and $R^5$ are independently hydrogen or $C_1$-$C_{20}$ alkyl, preferably hydrogen or methyl. More preferably, $R^1$, $R^2$, $R^3$, $R^4$, and $R^5$ are independently hydrogen or methyl, with the provision that at least one of $R^3$ and $R^4$ is methyl; and $R^5$ is methyl.

Preferably, $R^6$, $R^7$, $R^8$, $R^9$, $R^{10}$, $R^{11}$, $R^{12}$, and $R^{13}$ are independently hydrogen.

The transition metal compound of the formula 1 preferably includes the above-mentioned substituents with a view to controlling the electronic and steric environments around the metal.

In accordance with another embodiment of the present invention, there is provided a precursor for the transition metal compound of the formula 1 as represented by the following formula 2:

[Formula 2]

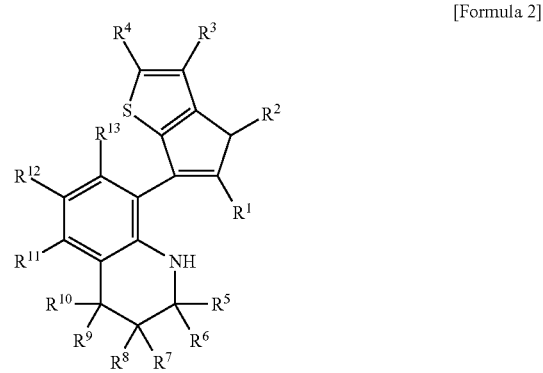

In the formula 2, $R^1$, $R^2$, $R^3$, $R^4$, $R^5$, $R^6$, $R^7$, $R^8$, $R^9$, and $R^{10}$ are independently hydrogen; $C_1$-$C_{20}$ alkyl with or without an acetal, ketal, or ether group; $C_2$-$C_{20}$ alkenyl with or without an acetal, ketal, or ether group; $C_1$-$C_{20}$ alkyl $C_6$-$C_{20}$ aryl with or without an acetal, ketal, or ether group; $C_6$-$C_{20}$ aryl $C_1$-$C_{20}$ alkyl with or without an acetal, ketal, or ether group; or $C_1$-$C_{20}$ silyl with or without an acetal, ketal, or ether group, where $R^1$ and $R^2$ can be linked to each other to form a ring; $R^3$ and $R^4$ can be linked to each other to form a ring, and at least two of $R^5$ to $R^{10}$ can be linked to each other to form a ring; and $R^{11}$, $R^{12}$, and $R^{13}$ are independently hydrogen; $C_1$-$C_{20}$ alkyl with or without an acetal, ketal, or ether group; $C_2$-$C_{20}$ alkenyl with or without an acetal, ketal, or ether group; $C_1$-$C_{20}$ alkyl $C_6$-$C_{20}$ aryl with or without an acetal, ketal, or ether group; $C_6$-$C_{20}$ aryl $C_1$-$C_{20}$ alkyl with or without an acetal, ketal, or ether group; $C_1$-$C_{20}$ silyl with or without an acetal, ketal, or ether group; $C_1$-$C_{20}$ alkoxy; or $C_6$-$C_{20}$ aryloxy, where $R^{11}$ and $R^{12}$, or $R^{12}$ and $R^{13}$ can be linked to each other to form a ring.

In the precursor for the transition metal compound by the formula 2, $R^1$, $R^2$, $R^3$, $R^4$, and $R^5$ are independently hydrogen or $C_1$-$C_{20}$ alkyl, preferably hydrogen or methyl. More preferably, $R^1$, $R^2$, $R^3$, $R^4$, and $R^5$ are independently hydrogen or methyl, with the provision that at least one of $R^3$ and $R^4$ is methyl; and $R^5$ is methyl.

Preferably, $R^6$, $R^7$, $R^8$, $R^9$, $R^{10}$, $R^{11}$, $R^{12}$, and $R^{13}$ are independently hydrogen.

In accordance with further another embodiment of the present invention, there is provided a method for preparing the precursor for transition metal compound represented by the formula 2, the method comprising: (a) reacting a tetrahydroquinoline derivative represented by the following formula 3 with alkyl lithium and adding carbon dioxide to prepare a compound represented by the following formula 4; and (b) reacting the compound of the formula 4 with alkyl lithium, adding a compound represented by the following formula 5, and then treating with an acid:

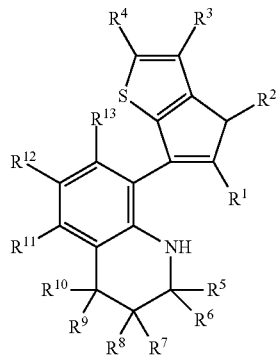

(Formula 2)

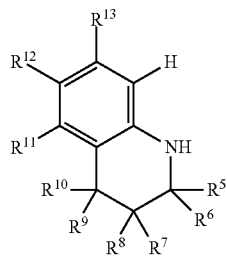

(Formula 3)

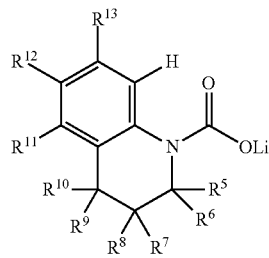

(Formula 4)

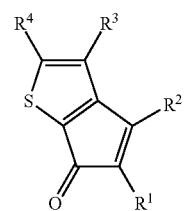

(Formula 5)

In the formulas 2, 3, 4 and 5, $R^1$, $R^2$, $R^3$, $R^4$, $R^5$, $R^6$, $R^7$, $R^8$, $R^9$, and $R^{10}$ are independently hydrogen; $C_1$-$C_{20}$ alkyl with or without an acetal, ketal, or ether group; $C_2$-$C_{20}$ alkenyl with or without an acetal, ketal, or ether group; $C_1$-$C_{20}$ alkyl $C_6$-$C_{20}$ aryl with or without an acetal, ketal, or ether group; $C_6$-$C_{20}$ aryl $C_1$-$C_{20}$ alkyl with or without an acetal, ketal, or ether group; or $C_1$-$C_{20}$ silyl with or without an acetal, ketal, or ether group, where $R^1$ and $R^2$ can be linked to each other to form a ring; $R^3$ and $R^4$ can be linked to each other to form a ring, and at least two of $R^5$ to $R^{10}$ can be linked to each other to form a ring; and $R^{11}$, $R^{12}$, and $R^{13}$ are independently hydrogen; $C_1$-$C_{20}$ alkyl with or without an acetal, ketal, or ether group; $C_2$-$C_{20}$ alkenyl with or without an acetal, ketal, or ether group; $C_1$-$C_{20}$ alkyl $C_6$-$C_{20}$ aryl with or without an acetal, ketal, or ether group; $C_6$-$C_{20}$ aryl $C_1$-$C_{20}$ alkyl with or without an acetal, ketal, or ether group; $C_1$-$C_{20}$ silyl with or without an acetal, ketal, or ether group; $C_1$-$C_{20}$ alkoxy; or $C_6$-$C_{20}$ aryloxy, where $R^{11}$ and $R^{12}$, or $R^{12}$ and $R^{13}$ can be linked to each other to form a ring.

The step (a) involves reacting a tetrahydroquinoline derivative of the formula 3 with alkyl lithium and then adding carbon dioxide to form a compound of the formula 4, which process can be achieved by the methods disclosed in the known documents (*Tetrahedron Lett.* 1985, 26, 5935; *Tetrahedron* 1986, 42, 2571; and *J. Chem. SC. Perkin Trans.* 1989, 16).

In the step (b), the compound of the formula 4 is reacted with alkyl lithium to activate deprotonation and produce an ortho-lithium compound, which is then reacted with a compound of the formula 5 and treated with an acid to obtain a precursor for transition metal compound of the formula 2.

The method of producing an ortho-lithium compound by reaction between the compound of the formula 4 and alkyl lithium is disclosed in known documents (*Organometallics* 2007, 27,6685; and Korean Patent Registration No. 2008-0065868). In the present invention, the ortho-lithium compound is reacted with a compound of the formula 5 to produce a precursor for transition metal compound of the formula 2.

The compound of the formula 5 can be prepared by a variety of known methods. For example, the following Scheme 3 can be used to prepare the precursor for the transition metal compound of the present invention with ease in a one-step process, which is economically beneficial by using inexpensive starting materials (*J. Organomet. Chem.*, 2005, 690, 4213).

[Scheme 3]

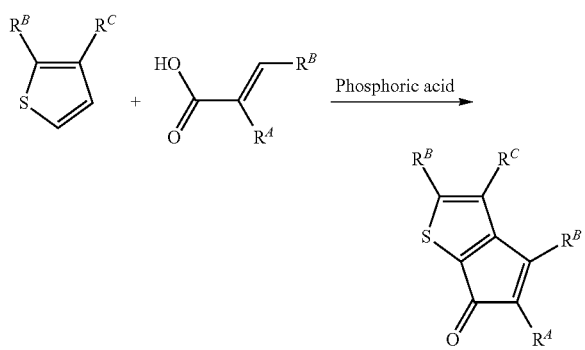

On the other hand, a variety of known methods can be employed to synthesize the transition metal compound of the formula 1 from the precursor for transition metal compound of the formula 2 obtained by the above-stated preparation method. The most common method of preparing the transition metal compound of the formula 1 involves adding 2 equivalents of alkyl lithium to the precursor for transition metal compound of the formula 2 to induce deprotonation for producing a dilithium compound of cyclopentadienyl anion and amide anion, and then adding $(Q^1)(Q^2)MCl_2$ to eliminate 2 equivalents of LiCl.

Another method involves reacting the compound of the formula 2 with $M(NMe_2)_4$ to eliminate 2 equivalents of $HNME_2$ and produce a transition metal compound of the formula 1, where both $Q^1$ and $Q^2$ are $NMe_2$, and then adding $Me_3SiCl$ or $Me_2SiCl_2$ to replace the $NMe_2$ ligand with a chlorine ligand.

In the compound of the formula 2, $R^1$, $R^2$, $R^3$, $R^4$, and $R^5$ are independently hydrogen or $C_1$-$C_{20}$ alkyl, preferably hydrogen or methyl. More preferably, $R^1$, $R^2$, $R^3$, $R^4$, and $R^5$ are independently hydrogen or methyl, with the provision that at least one of $R^3$ and $R^4$ is methyl; and $R^5$ is methyl. Preferably, $R^6$, $R^7$, $R^8$, $R^9$, $R^{10}$, $R^{11}$, $R^{12}$, and $R^{13}$ are independently hydrogen. In this regard, the precursor of the formula 2 with the above-mentioned substituents is desirable in terms of accessibility of a starting material and advantageous with a view to controlling the electronic and steric environments for the desired transition metal compound of the formula 1.

The preparation method for the transition metal compound is described more specifically with reference to the following examples.

In accordance with still another embodiment of the present invention, there is provided a catalyst composition comprising: a transition metal compound represented by the following formula 1; and at least one co-catalyst compound selected from the group consisting of compounds represented by the following formula 6, 7, or 8:

[Formula 1]

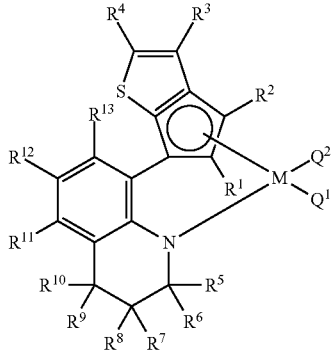

In the formula 1, M, $Q^1$, $Q^2$, $R^1$, $R^2$, $R^3$, $R^4$, $R^5$, $R^6$, $R^7$, $R^8$, $R^9$, $R^{10}$, $R^{11}$, $R^{12}$, and $R^{13}$ are as defined above.

$$-[Al(R^{61})-O]_a-$$ [Formula 6]

In the formula 6, $R^{61}$ is independently a halogen radical, a $C_1$-$C_{20}$ hydrocarbyl radical, or a halogen-substituted $C_1$-$C_{20}$ hydrocarbyl radical; and a is an integer of 2 or above.

$$D(R^{71})_3$$ [Formula 7]

In the formula 7, D is aluminum (Al) or boron (B); and $R^{71}$ is independently a halogen radical, a $C_1$-$C_{20}$ hydrocarbyl radical, or a halogen-substituted $C_1$-$C_{20}$ hydrocarbyl radical.

$$[L-H]^+[Z(A)_4]^- \text{ or } [L]^+[Z(A)_4]^-$$ [Formula 8]

In the formula 8, L is a neutral or cationic Lewis acid; Z is a Group 13 element; and A is independently a $C_6$-$C_{20}$ aryl or $C_1$-$C_{20}$ alkyl radical having at least one hydrogen atom substituted with a halogen radical, a $C_1$-$C_{20}$ hydrocarbyl radical, a $C_1$-$C_{20}$ alkoxy radical, or a $C_6$-$C_{20}$ aryloxy radical.

The compounds represented by the formula 6, 7, or 8 are widely used as a co-catalyst for the homogeneous Ziegler-Natta catalyst comprising a metallocene compound.

In the catalyst composition, the molar ratio (Ti:Al) of the co-catalyst compound of the formula 6 to the transition metal compound is preferably 1:100 to 1:20,000, more preferably 1:500 to 1:5,000.

The molar ratio (Ti:D) of the co-catalyst compound of the formula 7 to the transition metal compound, where D is boron (B), is preferably 1:1 to 1:10, more preferably 1:1 to 1:3. The molar ratio (Ti:D), where D is aluminum (Al), depends on the amount of water in the polymerization system and is preferably 1:1 to 1:1,000, more preferably 1:1 to 1:100.

The molar ratio (Ti:Z) of the co-catalyst compound of the formula 8 to the transition metal compound is preferably 1:1 to 1:10, more preferably 1:1 to 1:4.

In the catalyst composition, the molar ratio of the co-catalyst compound to the transition metal compound below the lower limit of the defined range possibly leads to failure to acquire the catalytic activity, while the molar ratio above the upper limit of the defined range increases the expense of the co-catalyst in preparation of resins.

In terms of the efficiency in activating the transition metal compound of the formula 1, the substituents are given as follows: in the formula 6, $R^{61}$ is methyl; in the formula 7, D is aluminum (Al), and $R^{71}$ is methyl or isobutyl; or D is boron (B), and $R^{71}$ is pentafluorophenyl; and in the formula 8, $[L-H]^+$ is a dimethylanilinium cation, $[Z(A)_4]^-$ is $[B(C_6F_5)_4]^-$, and $[L]^+$ is $[(C_6H_5)_3C]^+$.

In accordance with still another embodiment of the present invention, there is provided a method for preparing a polyolefin by polymerizing an olefin-based monomer in the presence of the catalyst composition.

The polyolefin can be prepared by reacting the catalyst composition with at least one olefin-based monomer. The olefin-based monomer is not specifically limited and preferably includes at least one monomer selected from the group consisting of ethylene, propylene, 1-butene, 1-hexene, 1-octene, and 1-decene.

The preparation method for polyolefin is more specifically described in the following examples of the present invention.

Hereinafter, a detailed description will be given as to the present invention in accordance with the preferred embodiments, which are given by way of illustration only and not intended to limit the scope of the present invention.

The synthesis procedures for the precursor and the transition metal compound were performed in the atmosphere of inert gas, such as nitrogen or argon, according to the following Schemes 4 and 5, using the standard Schlenk and glove box techniques.

The individual compounds in the Scheme 4 come in different substituents. The substituents are presented in the table given below the corresponding compound (for example, the compound D-2 denotes a compound having a hydrogen atom for $R^a$ and a methyl group for $R^b$ and $R^c$.).

In the Scheme 4, the compound C (C-1, C-2, or C-3) was synthesized by a known method (*J. Organomet. Chem.*, 2005, 690, 4213).

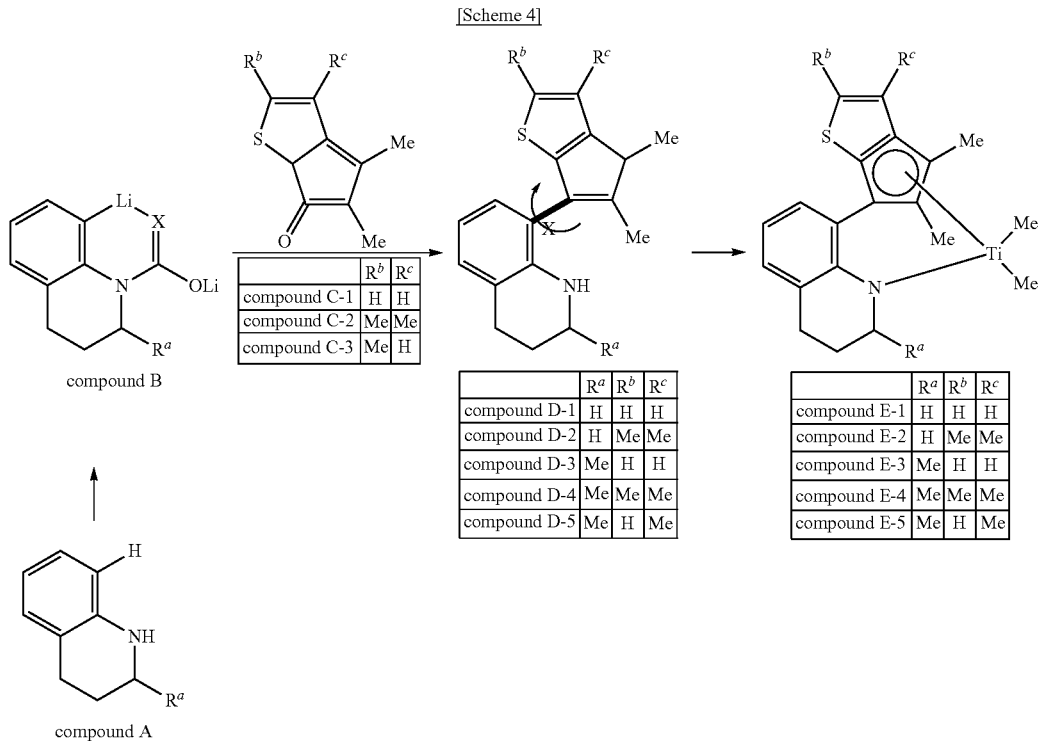

[Scheme 4]

Synthesis of Precursor and Transition Metal Compound

EXAMPLE 1

Synthesis of Precursor D-1

A Schlenk flask containing 1,2,3,4-tetrahydroquinoline (1.00 g, 7.51 mmol) and diethyl ether (16 ml) was cooled down in a cold bath at −78° C. and stirred while n-butyl lithium (3.0 mL, 7.5 mmol, 2.5 M hexane solution) was slowly added under the nitrogen atmosphere. After one-hour agitation at −78° C., the flask was gradually warmed up to the room temperature. A light yellowish solid precipitated, and the butane gas was removed through a bubbler. The flask was cooled down back to −78° C. and supplied with carbon dioxide. Upon injection of carbon dioxide, the slurry-type solution turned to a clear homogenous solution. After one-hour agitation at −78° C., the flask was gradually warmed up to −20° C. while the extra carbon dioxide was removed through the bubbler to remain a white solid as a precipitate.

Tetrahydrofuran (0.60 g, 8.3 mmol) and t-butyl lithium (4.9 mL, 8.3 mmol, 1.7 M pentane solution) were sequentially added at −20° C. in the nitrogen atmosphere, and the flask was agitated for about 2 hours. Subsequently, a tetrahydrofuran solution (19 mL) containing lithium chloride and the compound C-1 (1.06 g, 6.38 mmol) was added in the nitrogen atmosphere. The flask was agitated at −20° C. for one hour and then gradually warmed up to the room temperature. After one-hour agitation at the room temperature, water (15 mL) was added to terminate the reaction. The solution was moved to a separatory funnel to extract the organic phase. The extracted organic phase was put in a separatory funnel, and then hydrochloric acid (2 N, 40 mL) was added. After shaking the solution for about 2 minutes, an aqueous solution of sodium hydrocarbonate (60 mL) was slowly added to neutralize the solution. The organic phase was separated and removed of water with anhydrous magnesium sulfate to eliminate the solvent and yield a sticky product. The product thus obtained was purified by the silica gel column chromatography using a mixed solvent of hexane and ethylacetate (v/v, 50:1) to yield 77.2 mg of the desired compound (43% yield).

In the $^1$H NMR spectrum of the final product, there was observed a set of two signals at ratio of 1:1, resulting from the difficulty of rotating about the carbon-carbon bond (marked as a thick line in the Scheme 4) between phenylene and cyclopentadiene. In the following $^{13}$C NMR spectrum, the values in parenthesis are chemical shift values split due to the difficulty of rotation.

$^1$H NMR ($C_6D_6$): δ 7.22 and 7.17 (br d, J=7.2 Hz, 1H), 6.88 (s, 2H), 6.93 (d, J 7.2 Hz, 1H), 6.73 (br t, J=7.2 Hz, 1H), 3.84 and 3.80 (s, 1H, NH), 3.09 and 2.98 (q, J=8.0 Hz, 1H, CHMe), 2.90-2.75 (br, 2H, $CH_2$), 2.65-2.55 (br, 2H, $CH_2$), 1.87 (s, 3H, $CH_3$), 1.70-1.50 (m, 2H, $CH_2$), 1.16 (d, J=8.0 Hz, 3H, $CH_3$) ppm.

$^{13}$C NMR ($C_6D_6$): 151.64 (151.60), 147.74 (147.61), 146.68, 143.06, 132.60, 132.30, 129.85, 125.02, 121.85, 121.72, 119.74, 116.87, 45.86, 42.54, 28.39, 22.89, 16.32, 14.21 ppm.

EXAMPLE 2

Synthesis of Precursor D-2

The procedures were performed in the same manner as described in the synthesis of the compound D-1 in Example 1, excepting that the compound C-2 was used rather than the compound C-1. The yield was 53%.

In the $^1$H NMR spectrum of the final product, there was observed a set of two signals at ratio of 1:1, resulting from the difficulty of rotating about the carbon-carbon bond (marked as a thick line in the Scheme 4) between phenylene and cyclopentadiene.

$^1$H NMR (C$_6$D$_6$): δ 7.23 (d, J=7.2 Hz, 1H), 6.93 (d, J=7.2 Hz, 1H), 6.74 (br t, J=7.2 Hz, 1H), 4.00 and 3.93 (s, 1H, NH), 3.05 (br q, J=8.0 Hz, 1H, CHMe), 3.00-2.80 (br, 2H, CH$_2$), 2.70-2.50 (br, 2H, CH$_2$), 2.16 (s, 3H, CH$_3$), 2.04 (br s, 3H, CH$_3$), 1.91 (s, 3H, CH$_3$), 1.75-1.50 (m, 2H, CH$_2$), 1.21 (d, J=8.0 Hz, 3H, CH$_3$) ppm.

$^{13}$C NMR (C$_6$D$_6$): 151.60 (151.43), 145.56 (145.36), 143.08, 141.43, 132.90, 132.68, 132.43, 129.70, 121.63, 120.01, 116.77, 46.13, 42.58, 28.42, 22.97, 15.06, 14.19, 14.08, 12.70 ppm.

EXAMPLE 3

Synthesis of Precursor D-3

The procedures were performed in the same manner as described in the synthesis of the compound D-1 in Example 1, excepting that tetrahydroquinaldine was used rather than tetrahydroquinoline. The yield was 63%.

In the $^1$H NMR spectrum of the final product, a certain signal was split into a set of four signals at ratio of 1:1:1:1, resulting from the difficulty of rotating about the carbon-carbon bond (marked as a thick line in the Scheme 4) between phenylene and cyclopentadiene and isomerism pertaining to the existence of two chiral centers.

$^1$H NMR (C$_6$D$_6$): δ 7.33, 7.29, 7.22, and 7.17 (d, J=7.2 Hz, 1H), 6.97 (d, J=7.2 Hz, 1H), 6.88 (s, 2H), 6.80-6.70 (m, 1H), 3.93 and 3.86 (s, 1H, NH), 3.20-2.90 (m, 2H, NCHMe, CHMe), 2.90-2.50 (m, 2H, CH$_2$), 1.91, 1.89, and 1.86 (s, 3H, CH$_3$), 1.67-1.50 (m, 1H, CH$_2$), 1.50-1.33 (m, 1H, CH$_2$), 1.18, 1.16, and 1.14 (s, 3H, CH$_3$), 0.86, 0.85, and 0.80 (d, J=8.0 Hz, 3H, CH$_3$) ppm.

$^{13}$C NMR (C$_6$D$_6$): 151.67, 147.68 (147.56, 147.38), 147.06 (146.83, 146.28, 146.10), 143.01 (142.88), 132.99 (132.59), 132.36 (131.92), 129.69, 125.26 (125.08, 124.92, 124.83), 122.03, 121.69 (121.60, 121.28), 119.74 (119.68, 119.46), 117.13 (117.07, 116.79, 116.72), 47.90 (47.73), 46.04 (45.85), 31.00 (30.92, 30.50), 28.00 (27.83, 27.64), 23.25 (23.00), 16.38 (16.30), 14.63 (14.52, 14.18) ppm.

EXAMPLE 4

Synthesis of Precursor D-4

The procedures were performed in the same manner as described in the synthesis of the compound D-1 in Example 1, excepting that the compound C-2 and tetrahydroquinaldine were used rather than the compound C-1 and tetrahydroquinoline. The yield was 63%.

In the $^1$H NMR spectrum of the final product, a certain signal was split into a set of four signals at ratio of 1:1:1:1, resulting from the difficulty of rotating about the carbon-carbon bond (marked as a thick line in the Scheme 4) between phenylene and cyclopentadiene and isomerism pertaining to the existence of two chiral centers.

$^1$H NMR (C$_6$D$_6$): δ 7.32, 7.30, 7.22, and 7.19 (d, J=7.2 Hz, 1H), 6.97 (d, J=7.2 Hz, 1H), 6.85-6.65 (m, 1H), 4.10-3.90 (s, 1H, NH), 3.30-2.85 (m, 2H, NCHMe, CHMe), 2.85-2.50 (m, 2H, CH$_2$), 2.15 (s, 3H, CH$_3$), 2.02 (s, 3H, CH$_3$), 1.94, 1.92, and 1.91 (s, 3H, CH$_3$), 1.65-1.50 (m, 1H, CH$_2$), 1.50-1.33 (m, 1H, CH$_2$), 1.22, 1.21, 1.20, and 1.19 (s, 3H, CH$_3$), 1.10-0.75 (m, 3H, CH$_3$) ppm.

$^{13}$C NMR (C$_6$D$_6$): 151.67 (151.57), 145.58 (145.33, 145.20), 143.10 (143.00, 142.89), 141.62 (141.12), 134.08 (133.04), 132.84 (132.70, 136.60), 132.50 (132.08), 129.54, 121.52 (121.16), 119.96 (119.71), 117.04 (116.71), 47.90 (47.78), 46.29 (46.10), 31.05 (30.53), 28.02 (28.67), 23.37 (23.07), 15.22 (15.04), 14.87 (14.02, 14.21), 12.72 (12.67) ppm.

EXAMPLE 5

Synthesis of Precursor D-5

The procedures were performed in the same manner as described in the synthesis of the compound D-1 in Example 1, excepting that the compound C-3 and tetrahydroquinaldine were used rather than the compound C-1 and tetrahydroquinoline. The yield was 48%.

In the $^1$H NMR spectrum of the final product, a certain signal was split into a set of four signals at ratio of 1:1:1:1, resulting from the difficulty of rotating about the carbon-carbon bond (marked as a thick line in the Scheme 4) between phenylene and cyclopentadiene and isomerism pertaining to the existence of two chiral centers.

$^1$H NMR (C$_6$D$_6$): δ 7.32, 7.29, 7.22 and 7.18 (d, J=7.2 Hz, 1H), 6.96 (d, J=7.2 Hz, 1H), 6.84-6.68 (m, 1H), 6.60 (d, J=7.2 Hz, 1H), 4.00-3.92 (s, 1H, NH), 3.30-2.90 (m, 2H, NCHMe, CHMe), 2.90-2.55 (m, 2H, CH$_2$), 2.27 (s, 3H, CH$_3$), 1.94, 1.91 and 1.89 (s, 3H, CH$_3$), 1.65-1.54 (m, 1H, CH$_2$), 1.54-1.38 (m, 1H, CH$_2$), 1.23, 1.22, and 1.20 (s, 3H, CH$_3$), 1.00-0.75 (m, 3H, CH$_3$) ppm.

$^{13}$C NMR (C$_6$D$_6$): 151.51, 145.80, 145.64, 145.45, 144.40, 144.22, 143.76, 143.03, 142.91, 139.78, 139.69, 139.52, 133.12, 132.74, 132.52, 132.11, 129.59, 121.52, 121.19, 120.75, 120.47, 119.87, 119.69, 116.99, 116.76, 47.90, 47.77, 46.43, 46.23, 32.55, 30.98, 30.51, 27.95, 27.67, 23.67, 23.31, 23.06, 16.52, 15.01, 14.44, 14.05 ppm.

EXAMPLE 6

Synthesis of Transition Metal Compound E-1

In a dry box, the compound D-1 (0.10 g, 0.36 mmol) synthesized in Example 1 and dimethyl ether were put into a round-bottomed flask and cooled down to −30° C. N-butyl lithium (2.5 M hexane solution, 0.2 g, 0.71 mmol) was gradually added to the flask under agitation to activate the reaction at −30° C. for 2 hours. Warmed up to the room temperature, the flask was agitated for more 3 hours for the reaction. After cooled down back to −30° C., to the flask were added methyl lithium (1.6 M diethyl ether solution, 0.33 g, 0.71 mmol) and then TiCl$_4$.DME (DME: dimethoxyethane, 0.10 g, 0.36 mmol). The flask, while warmed up to the room temperature, was agitated for 3 hours and then removed of the solvent using a vacuum line. Pentane was used to extract the compound. The removal of the solvent produced 0.085 g of the final compound as a brownish powder (60% yield).

$^1$H NMR (C$_6$D$_6$): δ 7.09 (d, J=7.2 Hz, 1H), 6.91 (d, J=7.2 Hz, 1H), 6.81 (t, J=7.2 Hz, 1H), 6.74 (s, 2H), 4.55 (dt, J=14, 5.2 Hz, 1H, NCH$_2$), 4.38 (dt, J=14, 5.2 Hz, 1H, NCH$_2$), 2.50-2.30 (m, 2H, CH$_2$), 2.20 (s, 3H), 1.68 (s, 3H), 1.68 (quintet, J=5.2 Hz, CH$_2$), 0.72 (s, 3H, TiMe), 0.38 (s, 3H, TiMe) ppm.

$^{13}$C{$^1$H} NMR (C$_6$D$_6$): 161.46, 142.43, 140.10, 133.03, 130.41, 129.78, 127.57, 127.34, 121.37, 120.54, 120.51, 120.34, 112.52, 58.50, 53.73, 49.11, 27.59, 23.27, 13.19, 13.14 ppm.

EXAMPLE 7

Synthesis of Transition Metal Compound E-2

Figure 2:
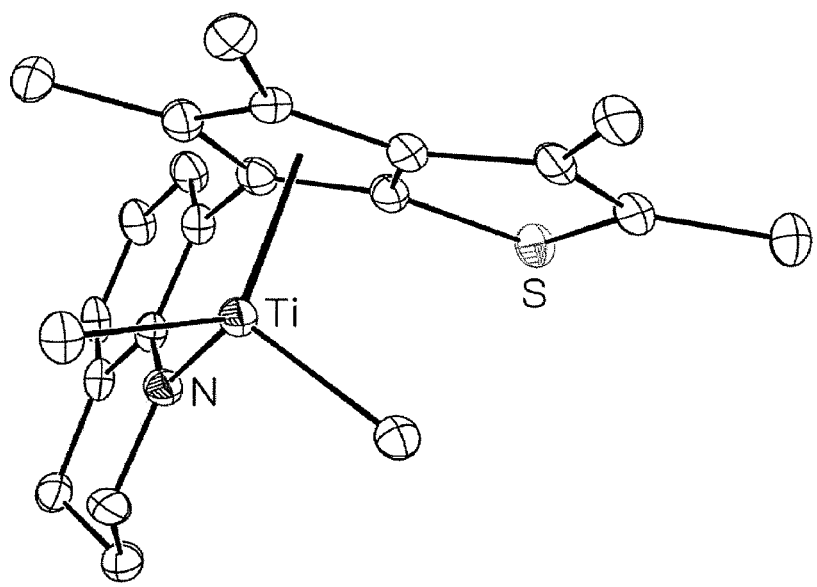
FIG. 2 is an illustration showing the structure of a transition metal compound (the compound E-2 of Example 7) according to another embodiment of the present invention.

The procedures were performed in the same manner as described in the synthesis of the compound E-1 in Example 6, excepting that the compound D-2 was used rather than the compound D-1. The yield was 53%. The structure of the transition metal compound E-2 is shown in FIG. 2.

$^1$H NMR (C$_6$D$_6$): δ 7.10 (d, J=7.2 Hz, 1H), 6.91 (d, J=7.2 Hz, 1H), 6.81 (t, J=7.2 Hz, 1H), 4.58 (dt, J=14, 5.2 Hz, 1H, NCH$_2$), 4.42 (dt, J=14, 5.2 Hz, 1H, NCH$_2$), 2.50-2.38 (m, 2H, CH$_2$), 2.32 (s, 3H), 2.11 (s, 3H), 2.00 (s, 3H), 1.71 (s, 3H), 1.67 (quintet, J=5.2 Hz, CH$_2$), 0.72 (s, 3H, TiMe), 0.38 (s, 3H, TiMe) ppm.

$^{13}$C{$^1$H} NMR (C$_6$D$_6$): 161.58, 141.36, 138.41, 137.20, 132.96, 129.70, 127.53, 127.39, 126.87, 121.48, 120.37, 120.30, 113.23, 56.50, 53.13, 49.03, 27.64, 23.34, 14.21, 13.40, 12.99, 12.94 ppm. Anal. Calc. (C$_{22}$H$_{27}$NSTi): C, 68.56; H, 7.06; N, 3.63. Found: C, 68.35 H, 7.37 N, 3.34%.

EXAMPLE 8

Synthesis of Transition Metal Compound E-3

The procedures were performed in the same manner as described in the synthesis of the compound E-1 in Example 6, excepting that the compound D-3 was used rather than the compound D-1. The yield was 51%. The final product was identified as a 1:1 mixture (the direction of the thiophene cyclic radical to the direction of the methyl radical on tetrahydroquinoline).

$^1$H NMR (C$_6$D$_6$): δ 7.11 and 7.08 (d, J=7.2 Hz, 1H), 6.96 and 6.95 (d, J=7.2 Hz, 1H), 6.82 and 6.81 (t, J=7.2 Hz, 1H), 6.77 and 6.76 (d, J=7.2 Hz, 1H), 6.74 and 6.73 (d, J=7.2 Hz, 1H), 5.42 (m, 1H, NCH), 2.75-2.60 (m, 1H, CH$_2$), 2.45-2.25 (m, 1H, CH$_2$), 2.24 and 2.18 (s, 3H), 1.73 and 1.63 (s, 3H), 1.85-1.50 (m, 2H, CH$_2$), 1.17 and 1.15 (d, J=4.8 Hz, 3H), 0.76 and 0.70 (s, 3H, TiMe), 0.42 and 0.32 (s, 3H, TiMe) ppm.

$^{13}$C{$^1$H} NMR (C$_6$D$_6$): 159.58, 159.28, 141.88, 141.00, 139.63, 138.98, 134.45, 130.85, 130.50, 129.59, 129.50, 129.47, 127.23, 127.20, 127.17, 127.11, 120.77, 120.70, 120.40, 120.00, 119.96, 119.91, 118.76, 118.57, 113.90, 110.48, 59.61, 56.42, 55.75, 51.96, 50.11, 49.98, 27.41, 27.11, 21.89, 20.09, 19.67, 12.94, 12.91, 12.65 ppm.

EXAMPLE 9

Synthesis of Transition Metal Compound E-4

The procedures were performed in the same manner as described in the synthesis of the compound E-1 in Example 6, excepting that the compound D-4 was used rather than the compound D-1. The yield was 57%. The final product was identified as a 1:1 mixture (the direction of the thiophene cyclic radical to the direction of the methyl radical on tetrahydroquinoline). The structure of the transition metal compound E-4 is shown in FIG. 1.

$^1$H NMR (C$_6$D$_6$): δ 7.12 and 7.10 (d, J=7.2 Hz, 1H), 6.96 and 6.94 (d, J=7.2 Hz, 1H), 6.82 and 6.81 (t, J=7.2 Hz, 1H), 5.45 (m, 1H, NCH), 2.75-2.60 (m, 1H, CH$_2$), 2.45-2.20 (m, 1H, CH$_2$), 2.34 and 2.30 (s, 3H), 2.10 (s, 3H), 1.97 (s, 3H), 1.75 and 1.66 (s, 3H), 1.85-1.50 (m, 2H, CH$_2$), 1.20 (d, J=6.8 Hz, 3H), 0.76 and 0.72 (s, 3H, TiMe), 0.44 and 0.35 (s, 3H, TiMe) ppm.

$^{13}$C{$^1$H} NMR (C$_6$D$_6$): 160.13, 159.86, 141.33, 140.46, 138.39, 137.67, 136.74, 134.83, 131.48, 129.90, 129.78, 127.69, 127.65, 127.60, 127.45, 126.87, 126.81, 121.34, 121.23, 120.21, 120.15, 119.15, 118.93, 114.77, 111.60, 57.54, 55.55, 55.23, 51.73, 50.43, 50.36, 27.83, 27.67, 22.37, 22.31, 20.53, 20.26, 14.29, 13.51, 13.42, 13.06, 12.80 ppm.

EXAMPLE 10

Synthesis of Transition Metal Compound E-5

The procedures were performed in the same manner as described in the synthesis of the compound E-1 in Example 6, excepting that the compound D-5 was used rather than the compound D-1. The yield was 57%. The final product was identified as a 1:1 mixture (the direction of the thiophene cyclic radical to the direction of the methyl radical on tetrahydroquinoline).

$^1$H NMR (C$_6$D$_6$): δ 7.12 and 7.09 (d, J=7.2 Hz, 1H), 6.96 and 6.94 (d, J=7.2 Hz, 1H), 6.82 and 6.80 (t, J=7.2 Hz, 1H), 6.47 and 6.46 (d, J=7.2 Hz, 1H), 6.45 and 6.44 (d, J=7.2 Hz, 1H), 5.44 (m, 1H, NCH), 2.76-2.60 (m, 1H, CH$_2$), 2.44-2.18 (m, 1H, CH$_2$), 2.28 and 2.22 (s, 3H), 2.09 (s, 3H), 1.74 and 1.65 (s, 3H), 1.88-1.48 (m, 2H, CH$_2$), 1.20 and 1.18 (d, J=7.2 Hz, 3H), 0.77 and 0.71 (s, 3H, TiMe), 0.49 and 0.40 (s, 3H, TiMe) ppm.

$^{13}$C{$^1$H} NMR (C$_6$D$_6$): 159.83, 159.52, 145.93, 144.90, 140.78, 139.93, 139.21, 138.86, 135.26, 131.56, 129.69, 129.57, 127.50, 127.46, 127.38, 127.24, 121.29, 121.16, 120.05, 119.96, 118.90, 118.74, 117.99, 117.74, 113.87, 110.38, 57.91, 55.31, 54.87, 51.68, 50.27, 50.12, 34.77, 27.58, 27.27, 23.10, 22.05, 20.31, 19.90, 16.66, 14.70, 13.11, 12.98, 12.68 ppm.

EXAMPLE 11

Synthesis of Transition Metal Compound E-6

The transition metal compound E-6 was synthesized according to the following Scheme 5.

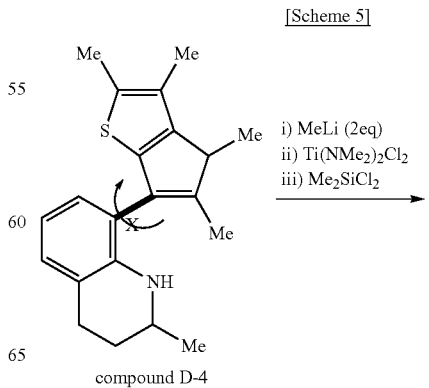

compound D-4

-continued

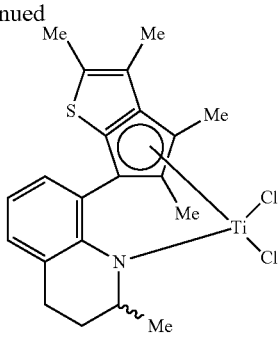

compound E-6

Methyl lithium (1.63 g, 3.55 mmol, 1.6 M diethyl ether solution) was added dropwise to a diethyl ether solution (10 mL) containing the compound D-4 (0.58 g, 1.79 mmol). The solution was agitated overnight at the room temperature and cooled down to −30° C. Then, Ti(NMe$_2$)$_2$Cl$_2$ (0.37 g, 1.79 mmol) was added at once. After 3-hour agitation, the solution was removed of all the solvent with a vacuum pump. The solid thus obtained was dissolved in toluene (8 mL), and Me$_2$SiCl$_2$ (1.16 g, 8.96 mmol) was added to the solution. The solution was agitated at 80° C. for 3 days and removed of the solvent with a vacuum pump to obtain a reddish solid compound (0.59 g, 75% yield). The $^1$H NMR spectrum showed the existence of two stereo-structural compounds at ratio of 2:1.

$^1$H NMR (C$_6$D$_6$): δ 7.10 (t, J=4.4 Hz, 1H), 6.90 (d, J=4.4 Hz, 2H), 5.27 and 5.22 (m, 1H, NCH), 2.54-2.38 (m, 1H, CH$_2$), 2.20-2.08 (m, 1H, CH$_2$), 2.36 and 2.35 (s, 3H), 2.05 and 2.03 (s, 3H), 1.94 and 1.93 (s, 3H), 1.89 and 1.84 (s, 3H), 1.72-1.58 (m, 2H, CH$_2$), 1.36-1.28 (m, 2H, CH$_2$), 1.17 and 1.14 (d, J=6.4, 3H, CH$_3$) ppm.

$^{13}$C{$^1$H} NMR (C$_6$D$_6$): 162.78, 147.91, 142.45, 142.03, 136.91, 131.12, 130.70, 130.10, 128.90, 127.17, 123.39, 121.33, 119.87, 54.18, 26.48, 21.74, 17.28, 14.46, 14.28, 13.80, 13.27 ppm.

Preparation of Polyolefin

EXAMPLES 12 to 15

Ethylene/1-hexene Copolymerization Using Catalyst Compound Containing One of Transition Metal Compounds E-1 to E-4 Activated with MAO A toluene solution of 1-hexene co-monomer (0.30 M, 1-hexene 0.76 g, 30 mL) was put into a high-pressure polymerization reactor in a dry box. Taken out of the dry box, the reactor was warmed up to 90° C. Each (0.50 μmol) of the compounds E-1 to E-4 synthesized in Examples 6 to 9 was mixed with methylaluminoxane (MAO) (7% Al toluene solution, 0.96 g, 2.5 mmol Al, Al/Ti=5,000) and further with toluene to make the total volume of the solution as 2 mL, thereby preparing an activated catalyst composition. The zirconium compound was insoluble in toluene but dissolved in combination with the methylaluminoxane (MAO). The activated catalyst composition thus obtained was injected into the reactor through a syringe. Then, ethylene was injected under pressure of 60 prig for 5-minute polymerization. The ethylene gas was ventilated, and 30 mL of acetone was added to terminate the reaction. The white solid thus obtained was filtered out and dried in a vacuum oven at 100° C. for one hour.

The polymerization results are presented in Table 1.

The compound E-3 in Example 14 had a high catalytic activity to yield 1.2 g of the desired polymer under the above-defined conditions. The copolymerization in this case is not desirable because almost all the 1-hexene was used up. Hence, the polymerization reaction was carried out for 2.5 minutes. The results are presented in Table 1.

The compound E-4 in Example 15 had an extremely high activity, leading to undesirable polymerization to yield 1.9 g of the desired polymer. Even when the polymerization time was reduced to a half, i.e., 2.5 minutes, the yielded amount of the product was 1.3 g, which resulted in undesired polymerization with extreme concentration gradient of 1-hexene. Finally, 0.88 g of the desired polymer was yielded when reducing the amount of the catalyst to 2.5 μmol and the polymerization time to 2.5 minutes. The polymerization results are presented in Table 1.

EXAMPLE 16

Ethylene/1-hexene Copolymerization Using Catalyst Compound Containing Transition Metal Compound E-4 Activated with Triisobutyl Aluminum and [PhC$_3$]$^+$[B(C$_6$F$_5$)$_4$]$^−$ The transition metal compound E-4 (0.50 μmol) was dissolved in toluene, and [PhC$_3$]$^+$[B(C$_6$F$_5$)$_4$]$^−$ (1.8 mg, 2.0 μmol, B/Ti=4) and triisobutyl aluminum (40 mg, 0.2 mmol) were sequentially added to the solution, which was then stood for 5 minutes. The catalyst composition thus activated was added into the reactor through a syringe. Then, the procedures for polymerization reaction were performed in the same manner as described in Examples 12 to 15 to yield the final polymer compound. The polymerization results are presented in Table 1.

COMPARATIVE EXAMPLE 1

Ethylene/1-hexene Copolymerization Using Catalyst Compound Containing Compound "a" Activated with MAO For comparison with the catalyst disclosed in Korean Patent Registration No. 820,542 and Korean Patent Publication No. 2008-65868 according to the prior art, the procedures for polymerization reaction were performed in the same manner as described in Examples 12 to 15, excepting that the following compound "a" was used.

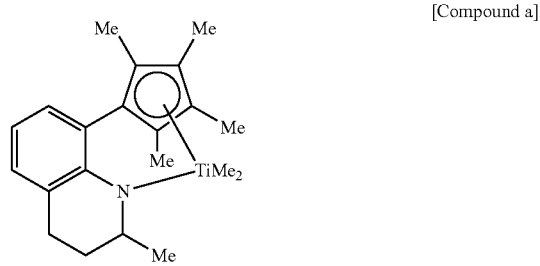

[Compound a]

COMPARATIVE EXAMPLE 2

Ethylene/1-hexene Copolymerization Using Catalyst Compound Containing Compound "a" Activated with Triisobutyl Aluminum and [PhC$_3$]$^+$[B(C$_6$F$_5$)$_4$]$^−$ The procedures for polymerization reaction were performed in the same manner as described in Example 16, excepting that the compound "a" was used as in Comparative Example 1. The polymerization results are presented in Table 1.

TABLE 1

|  | Transition metal compound (μmol) | Polymerization time (min) | Yield of polyolefin (g) | Activity[a] | [Hex][b] (mol %) | Mw[c] | Mw/Mn |
|---|---|---|---|---|---|---|---|
| Example 12 | Compound E-1 (0.50) | 5.0 | ~0 | ~0 |  |  |  |
| Example 13 | Compound E-2 (0.50) | 5.0 | 0.66 | 16 | 26 | 20000 | 2.2 |
| Example 14 | Compound E-3 (0.50) | 2.5 | 0.85 | 41 | 27 | 25000 | 2.3 |
| Example 15 | Compound E-4 (0.25) | 2.5 | 0.88 | 84 | 22 | 54000 | 2.2 |
| Example 16[d] | Compound E-4 (0.50) | 5.0 | 0.66 | 16 | 26 | 223000 | 2.5 |
| Comparative Example 1 | Compound "a" (0.25) | 5.0 | 0.68 | 33 | 32 | 30000 | 2.0 |
| Comparative Example 2[d] | Compound "a" (0.50) | 5.0 | 0.15 | 3.6 | 32 | 140000 | 2.1 |

[a](activity) unit $10^6$ g/mol Ti · h
[b]([Hex]) the quantity of 1-hexene in polyolefin chain ($^1$H NMR spectroscopy)
[c](Mw) weight average molecular weight measured by GPC using polystyrene as a reference
[d]polymerization using [Ph$_3$C[[B(C$_6$F$_5$)$_4$] as a co-catalyst As can be seen from the results of Table 1, the catalyst composition of the present invention had high catalytic activity and led to production of a polymer with high molecular weight. Particularly, Examples 15 and 16 showed excellences in terms of catalytic activity and molecular weight. The results also showed that the catalyst of the present invention had a catalytic activity at least 2.5 times higher and provided a polymer with molecular weight at least 1.6 to 1.8 time higher, demonstrating its considerable superiority to the conventional catalyst disclosed in Korean Patent Registration No. 820,542 and Korean Patent Publication No. 2008-65868 according to the prior art.

EXAMPLES 17 to 22

Ethylene/1-octene Copolymerization Using Catalyst Compound Containing One of Transition Metal Compounds E-2 to E-6 Activated with MAO The procedures were performed in the same manner as described in Examples 12 to 15, using a toluene solution of 1-octene co-monomer (0.30 M, 1-octene 1.0 g, 30 mL), any one (0.25 μmol) of the compounds E-2 to E-6, and methylaluminoxane (MAO) (7% Al toluene solution, 0.096 g, Al/Ti=1,000). Using a relatively small amount of MAO, (iBu)$_3$Al (0.20 mmol, Al/Ti=800) was additionally put into the reactor through a scavenger. The polymerization results are presented in Table 2.

EXAMPLE 23

Ethylene/1-octene Copolymerization Using Catalyst Compound Containing Transition Metal Compound E-4 Activated with Triisobutyl Aluminum and [PhC$_3$]$^+$[B(C$_6$F$_5$)$_4$]$^-$ The procedures were performed in the same manner as described in Example 16, using a toluene solution of 1-octene co-monomer (0.30 M, 1-octene 1.0 g, 30 mL), transition metal compound E-4 (0.25 μmol), [PhC$_3$]$^+$[B(C$_6$F$_5$)$_4$]$^-$ (1.0 μmol, B/Ti=4), and triisobutyl aluminum (0.20 mmol, Al/Ti=800). The polymerization results are presented in Table 2.

COMPARATIVE EXAMPLE 3

Ethylene/1-octene Copolymerization Using Catalyst Compound Containing Compound "a" Activated with MAO The procedures for polymerization reaction were performed in the same manner as described in Examples 17 to 22, excepting that the compound "a" was used as in Comparative Example 1. The polymerization results are presented in Table 2.

TABLE 2

|  | Transition metal compound (μmol) | Polymerization time (min) | Yield of polyolefin (g) | Activity[a] | [Oct][b] (mol %) | Mw[c] | Mw/Mn |
|---|---|---|---|---|---|---|---|
| Example 17 | Compound E-2 (0.25) | 3.0 | 0.20 | 16 | 22 | 132000 | 1.63 |
| Example 18 | Compound E-3 (0.25) | 3.0 | 0.25 | 20 | 25 | 87000 | 1.62 |
| Example 19 | Compound E-4 (0.25) | 3.0 | 0.78 | 62 | 14 | 157000 | 1.60 |
| Example 20 | Compound E-5 (0.25) | 3.0 | 0.68 | 54 | 20 | 153000 | 1.64 |
| Example 21 | Compound E-6 (0.25) | 3.0 | 0.63 | 50 | 22 | 152000 | 1.70 |

TABLE 2-continued

| | Transition metal compound (μmol) | Polymerization time (min) | Yield of polyolefin (g) | Activity[a] | [Oct][b] (mol %) | Mw[c] | Mw/Mn |
|---|---|---|---|---|---|---|---|
| Example 22[d] | Compound E-4 (0.50) | 3.0 | 0.91 | 36 | 21 | 104000 | 1.90 |
| Example 23[e] | Compound E-4 (0.25) | 3.0 | 0.84 | 67 | 21 | 295000 | 1.73 |
| Comparative Example 3 | Compound "a" (0.25) | 3.0 | 0.18 | 11 | 34 | 91000 | 1.51 |

[a](activity) unit $10^6$ g/mol Ti · h
[b]([Oct]) the quantity of 1-hexene in polyolefin chain ($^1$H NMR spectroscopy)
[c](Mw) weight average molecular weight measured by GPC using polystyrene as a reference
[d]polymerization using hexane as a solvent and MAO (Al/Ti = 500) as a co-catalyst
[e]polymerization using [Ph$_3$C][B(C$_6$F$_5$)$_4$] as a co-catalyst As can be seen from the results of Table 2, the catalyst composition of the present invention showed high catalytic activity and led to production of a polymer with high molecular weight under polymerization conditions using a relative small amount of MAO which is highly applicable in industrial use. Particularly, as shown in Examples 19 to 23, the compounds E-4, E-5, and E-6 showed high catalytic activity and enabled production of a polymer with high molecular weight. In relation to the catalyst composition of the present invention, the compound "a" of Comparative Example 3 as disclosed in Korean Patent Registration No. 820,542 and Korean Patent Publication No. 2008-65868 according to the prior art had a relatively low activity (as low as about 1/5) and provided a polymer with relatively low molecular weight under polymerization conditions using a smaller amount of MAO.

The invention claimed is:

1. A precursor for transition metal compound represented by the following formula 2:

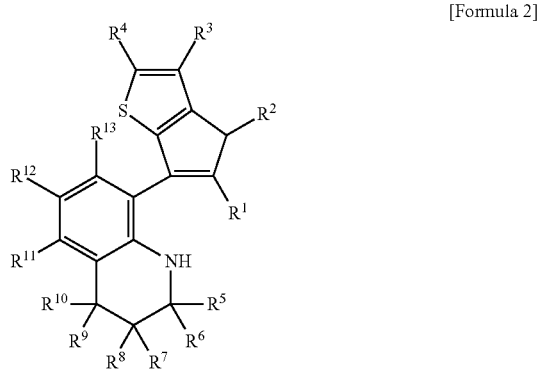

[Formula 2]

wherein $R^1$, $R^2$, $R^3$, $R^4$, $R^5$, $R^6$, $R^7$, $R^8$, $R^9$, and $R^{10}$ are independently hydrogen; $C_1$-$C_{20}$ alkyl with or without an acetal, ketal, or ether group; $C_2$-$C_{20}$ alkenyl with or without an acetal, ketal, or ether group; $C_1$-$C_{20}$ alkyl $C_6$-$C_{20}$ aryl with or without an acetal, ketal, or ether group; $C_6$-$C_{20}$ aryl $C_1$-$C_{20}$ alkyl with or without an acetal, ketal, or ether group; or $C_1$-$C_{20}$ silyl with or without an acetal, ketal, or ether group, wherein $R^1$ and $R^2$ can be linked to each other to form a ring; $R^3$ and $R^4$ can be linked to each other to form a ring, and at least two of $R^5$ to $R^{10}$ can be linked to each other to form a ring; and $R^{11}$, $R^{12}$, and $R^{13}$ are independently hydrogen; $C_1$-$C_{20}$ alkyl with or without an acetal, ketal, or ether group; $C_2$-$C_{20}$ alkenyl with or without an acetal, ketal, or ether group; $C_1$-$C_{20}$ alkyl $C_6$-$C_{20}$ aryl with or without an acetal, ketal, or ether group; $C_6$-$C_{20}$ aryl $C_1$-$C_{20}$ alkyl with or without an acetal, ketal, or ether group; $C_1$-$C_{20}$ silyl with or without an acetal, ketal, or ether group; $C_1$-$C_{20}$ alkoxy; or $C_6$-$C_{20}$ aryloxy, wherein $R^{11}$ and $R^{12}$, or $R^{12}$ and $R^{13}$ can be linked to each other to form a ring.

2. The precursor for transition metal compound as claimed in claim 1, wherein $R^1$, $R^2$, $R^3$, $R^4$, and $R^5$ are independently hydrogen or methyl; and $R^6$, $R^7$, $R^8$, $R^9$, $R^{10}$, $R^{11}$, $R^{12}$, and $R^{13}$ are independently hydrogen.

3. A method for preparing a precursor for transition metal compound represented by the following formula 2, the method comprising:

(a) reacting a tetrahydroquinoline derivative represented by the following formula 3 with alkyl lithium and adding carbon dioxide to prepare a compound represented by the following formula 4; and (b) reacting the compound of the formula 4 with alkyl lithium, adding a compound represented by the following formula 5, and then treating with an acid:

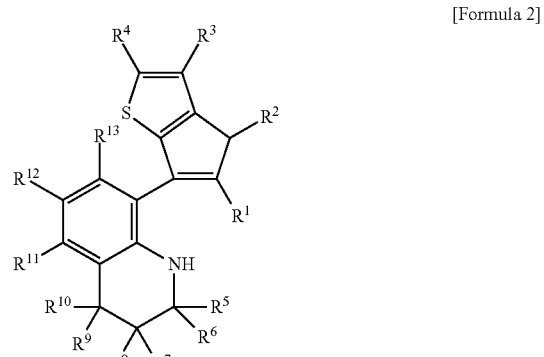

[Formula 2]

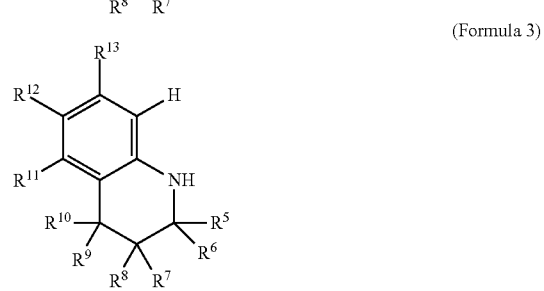

(Formula 3)

-continued

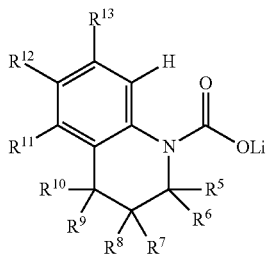
(Formula 4)

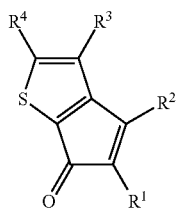
(Formula 5)

wherein $R^1$, $R^2$, $R^3$, $R^4$, $R^5$, $R^6$, $R^7$, $R^8$, $R^9$, and $R^{10}$ are independently hydrogen; $C_1$-$C_{20}$ alkyl with or without an acetal, ketal, or ether group; $C_2$-$C_{20}$ alkenyl with or without an acetal, ketal, or ether group; $C_1$-$C_{20}$ alkyl $C_6$-$C_{20}$ aryl with or without an acetal, ketal, or ether group; $C_6$-$C_{20}$ aryl $C_1$-$C_{20}$ alkyl with or without an acetal, ketal, or ether group; or $C_1$-$C_{20}$ silyl with or without an acetal, ketal, or ether group, wherein $R^1$ and $R^2$ can be linked to each other to form a ring; $R^3$ and $R^4$ can be linked to each other to form a ring, and at least two of $R^5$ to $R^{10}$ can be linked to each other to form a ring; and $R^{11}$, $R^{12}$, and $R^{13}$ are independently hydrogen; $C_1$-$C_{20}$ alkyl with or without an acetal, ketal, or ether group; $C_2$-$C_{20}$ alkenyl with or without an acetal, ketal, or ether group; $C_1$-$C_{20}$ alkyl $C_6$-$C_{20}$ aryl with or without an acetal, ketal, or ether group; $C_6$-$C_{20}$ aryl $C_1$-$C_{20}$ alkyl with or without an acetal, ketal, or ether group; $C_1$-$C_{20}$ silyl with or without an acetal, ketal, or ether group; $C_1$-$C_{20}$ alkoxy; or $C_6$-$C_{20}$ aryloxy, wherein $R^{11}$ and $R^{12}$, or $R^{12}$ and $R^{13}$ can be linked to each other to form a ring.

4. The method as claimed in claim 3, wherein $R^1$, $R^2$, $R^3$, $R^4$, and $R^5$ are independently hydrogen or methyl; and $R^6$, $R^7$, $R^8$, $R^9$, $R^{10}$, $R^{11}$, $R^{12}$, and $R^{13}$ are independently hydrogen.

* * * * *